United States Patent
Scharf et al.

(10) Patent No.: US 12,178,582 B2
(45) Date of Patent: Dec. 31, 2024

(54) SYSTEMS AND METHODS FOR CALCULATING PATIENT INFORMATION

(71) Applicant: Acutus Medical, Inc., Carlsbad, CA (US)

(72) Inventors: Gunter Scharf, Gockhausen (CH); Christoph Scharf, Horgen (CH); Derrick Ren-yu Chou, San Diego, CA (US); Graydon Ernest Beatty, Carlsbad, CA (US); R. Maxwell Flaherty, Topsfield, MA (US); J. Christopher Flaherty, Auburndale, FL (US)

(73) Assignee: ACUTUS MEDICAL, INC., Carlsbad, CA (US)

( * ) Notice: Subject to any disclaimer, the term of this patent is extended or adjusted under 35 U.S.C. 154(b) by 794 days.

(21) Appl. No.: 17/275,690

(22) PCT Filed: Nov. 8, 2019

(86) PCT No.: PCT/US2019/060433
§ 371 (c)(1),
(2) Date: Mar. 12, 2021

(87) PCT Pub. No.: WO2020/097438
PCT Pub. Date: May 14, 2020

(65) Prior Publication Data
US 2022/0095980 A1   Mar. 31, 2022

Related U.S. Application Data

(60) Provisional application No. 62/757,961, filed on Nov. 9, 2018.

(51) Int. Cl.
  *A61B 5/02*   (2006.01)
  *A61B 5/00*   (2006.01)
  (Continued)

(52) U.S. Cl.
  CPC ............ *A61B 5/283* (2021.01); *A61B 5/0538* (2013.01); *A61B 5/256* (2021.01); *A61B 5/265* (2021.01);
  (Continued)

(58) Field of Classification Search
  CPC ... A61B 5/0006; A61B 5/0033; A61B 5/0036; A61B 5/004; A61B 5/0044;
  (Continued)

(56) References Cited

U.S. PATENT DOCUMENTS

| 4,173,228 A | 11/1979 | Van Steenwyk et al. |
| 4,841,977 A | 6/1989 | Griffith et al. |

(Continued)

FOREIGN PATENT DOCUMENTS

| CA | 2825736 | 5/2008 |
| CA | 2829626 | 9/2012 |

(Continued)

OTHER PUBLICATIONS

Chinese Office Action dated Sep. 8, 2021 issued in corresponding Chinese Application No. 201680040709.1.
(Continued)

*Primary Examiner* — George Manuel
(74) *Attorney, Agent, or Firm* — Onello & Mello, LLP

(57) ABSTRACT

Provided herein are systems and methods for calculating patient information. The method includes determining a transfer matrix, recording electric potentials via a first set of recording electrodes located at a first set of recording locations to create a first set of recorded signals, and calculating patient information for a set of target locations by applying the transfer matrix to the first set of recorded signals. The transfer matrix is a characterization of electrical properties of tissue between the first set of recording locations and the set of target locations.

26 Claims, 3 Drawing Sheets

(51) Int. Cl.

| | | |
|---|---|---|
| *A61B 5/0538* | (2021.01) | |
| *A61B 5/256* | (2021.01) | |
| *A61B 5/265* | (2021.01) | |
| *A61B 5/266* | (2021.01) | |
| *A61B 5/283* | (2021.01) | |
| *A61B 5/367* | (2021.01) | |
| *A61B 5/024* | (2006.01) | |
| *A61B 5/0245* | (2006.01) | |
| *A61B 5/24* | (2021.01) | |
| *A61B 5/257* | (2021.01) | |
| *A61B 5/28* | (2021.01) | |
| *A61B 5/307* | (2021.01) | |
| *A61B 5/308* | (2021.01) | |
| *A61B 5/318* | (2021.01) | |
| *A61B 5/346* | (2021.01) | |

(52) U.S. Cl.
 CPC ............ *A61B 5/266* (2021.01); *A61B 5/367* (2021.01); *A61B 5/7475* (2013.01); *A61B 5/0006* (2013.01); *A61B 5/0033* (2013.01); *A61B 5/0036* (2018.08); *A61B 5/004* (2013.01); *A61B 5/0044* (2013.01); *A61B 5/0048* (2013.01); *A61B 5/0082* (2013.01); *A61B 5/0084* (2013.01); *A61B 5/02* (2013.01); *A61B 5/024* (2013.01); *A61B 5/02427* (2013.01); *A61B 5/02438* (2013.01); *A61B 5/0245* (2013.01); *A61B 5/24* (2021.01); *A61B 5/257* (2021.01); *A61B 5/28* (2021.01); *A61B 5/307* (2021.01); *A61B 5/308* (2021.01); *A61B 5/318* (2021.01); *A61B 5/346* (2021.01); *A61B 5/6802* (2013.01)

(58) Field of Classification Search
 CPC ... A61B 5/0048; A61B 5/0082; A61B 5/0084; A61B 5/02; A61B 5/024; A61B 5/02427; A61B 5/02438; A61B 5/0245; A61B 5/0535; A61B 5/0538; A61B 5/24; A61B 5/256; A61B 5/257; A61B 5/265; A61B 5/266; A61B 5/28; A61B 5/282; A61B 5/283; A61B 5/287; A61B 5/307; A61B 5/308; A61B 5/318; A61B 5/346; A61B 5/367; A61B 5/6802; A61B 5/7207; A61B 5/7475
 See application file for complete search history.

(56) References Cited

U.S. PATENT DOCUMENTS

| | | |
|---|---|---|
| 5,041,973 A | 8/1991 | Lebron et al. |
| 5,156,151 A | 10/1992 | Imran |
| 5,293,868 A | 3/1994 | Nardella |
| 5,482,472 A | 1/1996 | Garoni et al. |
| 5,499,981 A | 3/1996 | Kordis |
| 5,555,883 A | 9/1996 | Avitall |
| 5,595,183 A | 1/1997 | Swanson et al. |
| 5,601,084 A | 2/1997 | Sheehan et al. |
| 5,647,367 A | 7/1997 | Lum et al. |
| 5,662,108 A | 9/1997 | Budd et al. |
| 5,722,402 A | 3/1998 | Swanson et al. |
| 5,722,416 A | 3/1998 | Swanson et al. |
| 5,740,808 A | 4/1998 | Panescu et al. |
| 5,749,833 A | 5/1998 | Hakki et al. |
| 5,759,158 A | 6/1998 | Swanson |
| 5,782,239 A | 7/1998 | Webster, Jr. |
| 5,795,298 A | 8/1998 | Vesley et al. |
| 5,795,299 A | 8/1998 | Eaton et al. |
| 5,820,568 A | 10/1998 | Willis |
| 5,830,144 A | 11/1998 | Vesely |
| 5,846,198 A | 12/1998 | Killmann |
| 5,876,336 A | 3/1999 | Swanson et al. |
| 5,928,228 A | 7/1999 | Kordis et al. |
| 5,944,022 A | 8/1999 | Nardella et al. |
| 5,968,040 A | 10/1999 | Swanson et al. |
| 6,014,590 A | 1/2000 | Whayne et al. |
| 6,024,703 A | 2/2000 | Zanelli et al. |
| 6,066,096 A | 5/2000 | Smith et al. |
| 6,086,532 A | 7/2000 | Panescu et al. |
| 6,107,699 A | 8/2000 | Swanson |
| 6,115,626 A | 9/2000 | Whayne et al. |
| 6,187,032 B1 | 2/2001 | Ohyu et al. |
| 6,188,928 B1 | 2/2001 | Noren et al. |
| 6,216,027 B1 | 4/2001 | Willis et al. |
| 6,216,043 B1 | 4/2001 | Swanson et al. |
| 6,240,307 B1 | 5/2001 | Beatty et al. |
| 6,301,496 B1 | 10/2001 | Reisfeld |
| 6,396,198 B1 | 5/2002 | Okimura et al. |
| 6,400,981 B1 | 6/2002 | Govari |
| 6,490,474 B1 | 12/2002 | Willis et al. |
| 6,514,249 B1 | 2/2003 | Maguire et al. |
| 6,556,695 B1 | 4/2003 | Packer et al. |
| 6,574,492 B1 | 6/2003 | Ben-Haim et al. |
| 6,640,119 B1 | 10/2003 | Budd et al. |
| 6,695,785 B2 | 2/2004 | Brisken et al. |
| 6,716,166 B2 | 4/2004 | Govari |
| 6,728,562 B1 | 4/2004 | Budd et al. |
| 6,772,004 B2 | 8/2004 | Rudy |
| 6,773,402 B2 | 8/2004 | Govari et al. |
| 6,824,515 B2 | 11/2004 | Suorsa et al. |
| 6,826,420 B1 | 11/2004 | Beatty et al. |
| 6,826,421 B1 | 11/2004 | Beatty et al. |
| 6,839,588 B1 | 1/2005 | Rudy |
| 6,895,267 B2 | 5/2005 | Panescu et al. |
| 6,939,309 B1 | 9/2005 | Beatty et al. |
| 6,950,689 B1 | 9/2005 | Willis et al. |
| 6,970,733 B2 | 11/2005 | Willis et al. |
| 6,978,168 B2 | 12/2005 | Beatty et al. |
| 6,990,370 B1 | 1/2006 | Beatty et al. |
| 7,187,964 B2 | 3/2007 | Khoury |
| 7,187,973 B2 | 3/2007 | Hauck |
| 7,258,674 B2 | 8/2007 | Hillstead et al. |
| 7,263,397 B2 | 8/2007 | Hauck et al. |
| 7,285,094 B2 | 10/2007 | Nohara et al. |
| 7,285,119 B2 | 10/2007 | Stewart et al. |
| 7,289,843 B2 | 10/2007 | Beatty et al. |
| 7,291,146 B2 | 11/2007 | Steinke et al. |
| 7,351,914 B2 | 4/2008 | Kaneto et al. |
| 7,479,141 B2 | 1/2009 | Kleen et al. |
| 7,505,810 B2 | 3/2009 | Harlev et al. |
| 7,536,218 B2 | 5/2009 | Govari et al. |
| 7,573,182 B2 | 8/2009 | Savage |
| 7,689,261 B2 | 3/2010 | Mohr et al. |
| 7,766,838 B2 | 8/2010 | Yagi et al. |
| 7,841,986 B2 | 11/2010 | He et al. |
| 7,918,793 B2 | 4/2011 | Altmann et al. |
| 7,953,475 B2 | 5/2011 | Harlev et al. |
| 8,103,327 B2 | 1/2012 | Harlev et al. |
| 8,147,486 B2 | 4/2012 | Honour et al. |
| 8,150,499 B2 | 4/2012 | Gelbart et al. |
| 8,175,680 B2 | 5/2012 | Panescu |
| 8,200,314 B2 | 6/2012 | Bladen et al. |
| 8,208,998 B2 | 6/2012 | Beatty et al. |
| 8,221,411 B2 | 7/2012 | Francischelli et al. |
| 8,233,972 B2 | 7/2012 | Zhang |
| 8,311,613 B2 | 11/2012 | Danehorn |
| 8,320,711 B2 | 11/2012 | Altmann et al. |
| 8,346,339 B2 | 1/2013 | Kordis et al. |
| 8,360,786 B2 | 1/2013 | Duryea |
| 8,364,234 B2 | 1/2013 | Kordis et al. |
| 8,412,307 B2 | 4/2013 | Willis et al. |
| 8,417,313 B2 | 4/2013 | Scharf et al. |
| 8,428,690 B2 | 4/2013 | Li et al. |
| 8,447,377 B2 | 5/2013 | Harlev et al. |
| 8,454,596 B2 | 6/2013 | Ma et al. |
| 8,465,433 B2 | 6/2013 | Zwirn |
| 8,478,388 B2 | 7/2013 | Nguyen et al. |
| 8,512,255 B2 | 8/2013 | Scharf et al. |
| 8,571,647 B2 | 10/2013 | Harlev et al. |
| 8,700,119 B2 | 4/2014 | Scharf et al. |

(56) References Cited

U.S. PATENT DOCUMENTS

| | | |
|---|---|---|
| 8,755,861 B2 | 6/2014 | Harlev et al. |
| 8,825,130 B2 | 9/2014 | Just et al. |
| 8,825,134 B2 | 9/2014 | Danehorn |
| 8,918,158 B2 | 12/2014 | Scharf et al. |
| 8,934,988 B2 | 1/2015 | Persson et al. |
| 8,948,837 B2 | 2/2015 | Harlev et al. |
| 8,968,299 B2 | 3/2015 | Kauphusman et al. |
| 8,979,839 B2 | 3/2015 | De La Rama et al. |
| 8,989,842 B2 | 3/2015 | Li et al. |
| 9,011,423 B2 | 4/2015 | Brewster et al. |
| 9,023,027 B2 | 5/2015 | Bar-Tal et al. |
| 9,026,196 B2 | 5/2015 | Curran et al. |
| 9,031,642 B2 | 5/2015 | Ghosh |
| 9,037,259 B2 | 5/2015 | Mathur |
| 9,044,245 B2 | 6/2015 | Condie et al. |
| 9,113,807 B2 | 8/2015 | Koyrakh et al. |
| 9,167,982 B2 | 10/2015 | Scharf et al. |
| 9,186,081 B2 | 11/2015 | Afonso et al. |
| 9,186,212 B2 | 11/2015 | Nabutovsky et al. |
| 9,192,318 B2 | 11/2015 | Scharf et al. |
| 9,220,432 B2 | 12/2015 | Bukhman |
| 9,241,687 B2 | 1/2016 | Mcgee |
| 9,351,789 B2 | 5/2016 | Novichenok et al. |
| D758,596 S | 6/2016 | Perryman et al. |
| 9,358,398 B2 | 6/2016 | Moffitt et al. |
| 9,380,953 B2 | 7/2016 | Houben et al. |
| 9,474,486 B2 | 10/2016 | Eliason et al. |
| 9,480,525 B2 | 11/2016 | Lopes et al. |
| 9,486,355 B2 | 11/2016 | Gustus et al. |
| 9,492,227 B2 | 11/2016 | Lopes et al. |
| 9,492,228 B2 | 11/2016 | Lopes et al. |
| 9,498,192 B2 | 11/2016 | Hashimshony et al. |
| 9,504,395 B2 | 11/2016 | Scharf et al. |
| 9,526,573 B2 | 12/2016 | Lopes et al. |
| 9,549,708 B2 | 1/2017 | Mercanzini et al. |
| 9,579,149 B2 | 2/2017 | Kelly et al. |
| D782,686 S | 3/2017 | Werneth et al. |
| 9,585,588 B2 | 3/2017 | Marecki et al. |
| 9,603,651 B2 | 3/2017 | Ghosh |
| 9,610,024 B2 | 4/2017 | Scharf et al. |
| 9,675,266 B2 | 6/2017 | Afonso et al. |
| 9,713,730 B2 | 7/2017 | Mathur et al. |
| 9,717,555 B2 | 8/2017 | Chan et al. |
| 9,717,559 B2 | 8/2017 | Ditter et al. |
| 9,730,602 B2 | 8/2017 | Harlev et al. |
| 9,757,044 B2 | 9/2017 | Scharf et al. |
| 9,827,039 B2 | 11/2017 | Dandler et al. |
| 9,901,303 B2 | 2/2018 | Olson |
| 9,913,589 B2 | 3/2018 | Scharf et al. |
| 9,968,268 B2 | 5/2018 | Scharf et al. |
| 10,004,459 B2 | 6/2018 | Werneth et al. |
| 10,028,706 B2 | 7/2018 | Brockway et al. |
| 10,082,395 B2 | 9/2018 | Koyrakh et al. |
| 10,201,311 B2 | 2/2019 | Chou et al. |
| 10,296,707 B2 | 5/2019 | Passerini et al. |
| 10,405,828 B2 | 9/2019 | Deladi et al. |
| 10,593,234 B2 | 3/2020 | Zhu et al. |
| 10,653,318 B2 | 5/2020 | Welsh et al. |
| 2001/0007070 A1 | 7/2001 | Stewart et al. |
| 2002/0026118 A1 | 2/2002 | Govari |
| 2002/0045810 A1 | 4/2002 | Ben-Haim |
| 2002/0099292 A1 | 7/2002 | Brisken et al. |
| 2002/0128565 A1 | 9/2002 | Rudy |
| 2002/0165441 A1 | 11/2002 | Coleman et al. |
| 2003/0036696 A1 | 2/2003 | Willis et al. |
| 2003/0065271 A1 | 4/2003 | Khoury |
| 2003/0078494 A1 | 4/2003 | Panescu et al. |
| 2003/0120318 A1 | 6/2003 | Hauck |
| 2003/0153907 A1 | 8/2003 | Suorsa et al. |
| 2003/0158477 A1 | 8/2003 | Panescu |
| 2003/0163046 A1 | 8/2003 | Nohara et al. |
| 2003/0176799 A1 | 9/2003 | Beatty et al. |
| 2003/0231789 A1 | 12/2003 | Willis et al. |
| 2003/0236466 A1 | 12/2003 | Tarjan et al. |
| 2004/0039312 A1 | 2/2004 | Hillstead et al. |
| 2004/0082870 A1 | 4/2004 | Rudy et al. |
| 2004/0082948 A1 | 4/2004 | Stewart et al. |
| 2004/0113498 A1 | 6/2004 | Kroenke |
| 2004/0254437 A1 | 12/2004 | Hauck et al. |
| 2005/0059880 A1 | 3/2005 | Mathias et al. |
| 2005/0101874 A1 | 5/2005 | Beatty et al. |
| 2005/0113665 A1 | 5/2005 | Mohr et al. |
| 2005/0148836 A1 | 7/2005 | Kleen et al. |
| 2005/0203375 A1 | 9/2005 | Willis et al. |
| 2006/0052716 A1 | 3/2006 | Beatty et al. |
| 2006/0058663 A1 | 3/2006 | Willis et al. |
| 2006/0058676 A1 | 3/2006 | Yagi et al. |
| 2006/0058692 A1 | 3/2006 | Beatty et al. |
| 2006/0058693 A1 | 3/2006 | Beatty et al. |
| 2006/0084884 A1 | 4/2006 | Beatty et al. |
| 2006/0084970 A1 | 4/2006 | Beatty et al. |
| 2006/0084971 A1 | 4/2006 | Beatty et al. |
| 2006/0084972 A1 | 4/2006 | Beatty et al. |
| 2006/0116576 A1 | 6/2006 | McGee et al. |
| 2006/0244177 A1 | 11/2006 | Kaneto et al. |
| 2007/0016007 A1 | 1/2007 | Govari et al. |
| 2007/0055150 A1 | 3/2007 | Donaldson et al. |
| 2007/0060832 A1 | 3/2007 | Levin |
| 2007/0083194 A1 | 4/2007 | Kunis et al. |
| 2007/0106146 A1 | 5/2007 | Altmann et al. |
| 2007/0167722 A1 | 7/2007 | Bladen et al. |
| 2007/0232949 A1 | 10/2007 | Saksena |
| 2008/0009758 A1 | 1/2008 | Voth |
| 2008/0146937 A1 | 6/2008 | Lee et al. |
| 2008/0287777 A1 | 11/2008 | Li et al. |
| 2008/0319297 A1 | 12/2008 | Danehorn |
| 2009/0024086 A1 | 1/2009 | Zhang et al. |
| 2009/0076483 A1 | 3/2009 | Danehorn |
| 2009/0082691 A1 | 3/2009 | Denison et al. |
| 2009/0131930 A1 | 5/2009 | Gelbart et al. |
| 2009/0143651 A1 | 6/2009 | Kallback et al. |
| 2009/0148012 A1 | 6/2009 | Altmann et al. |
| 2009/0171274 A1 | 7/2009 | Harlev et al. |
| 2009/0264781 A1 | 10/2009 | Scharf et al. |
| 2010/0023004 A1 | 1/2010 | Francischelli et al. |
| 2010/0076426 A1 | 3/2010 | de la Rama et al. |
| 2010/0094279 A1 | 4/2010 | Kauphusman et al. |
| 2010/0168578 A1 | 7/2010 | Garson, Jr. et al. |
| 2010/0256627 A1 | 10/2010 | Ma et al. |
| 2010/0279263 A1 | 11/2010 | Duryea |
| 2010/0286551 A1 | 11/2010 | Harlev et al. |
| 2010/0298690 A1 | 11/2010 | Scharf et al. |
| 2011/0045130 A1 | 2/2011 | Edens et al. |
| 2011/0077526 A1 | 3/2011 | Zwirn |
| 2011/0092809 A1 | 4/2011 | Nguyen et al. |
| 2011/0118726 A1 | 5/2011 | De La Rama et al. |
| 2011/0125172 A1 | 5/2011 | Gelbart et al. |
| 2011/0144510 A1 | 6/2011 | Ryu et al. |
| 2011/0172658 A1 | 7/2011 | Gelbart et al. |
| 2011/0201951 A1 | 8/2011 | Zhang |
| 2011/0213231 A1 | 9/2011 | Hall et al. |
| 2011/0230775 A1 | 9/2011 | Barley et al. |
| 2011/0270237 A1 | 11/2011 | Werneth et al. |
| 2012/0078077 A1 | 3/2012 | Harlev et al. |
| 2012/0082969 A1 | 4/2012 | Schwartz et al. |
| 2012/0123296 A1 | 5/2012 | Hashimshony et al. |
| 2012/0136231 A1 | 5/2012 | Markel |
| 2012/0143298 A1 | 6/2012 | Just et al. |
| 2012/0165667 A1 | 6/2012 | Altmann et al. |
| 2012/0172702 A1 | 7/2012 | Koyrakh et al. |
| 2012/0172859 A1 | 7/2012 | Condie et al. |
| 2012/0184863 A1 | 7/2012 | Harlev et al. |
| 2012/0265054 A1 | 10/2012 | Olson |
| 2012/0271138 A1 | 10/2012 | Kordis et al. |
| 2012/0271139 A1 | 10/2012 | Kordis et al. |
| 2012/0277574 A1 | 11/2012 | Panescu |
| 2012/0302912 A1 | 11/2012 | Moffitt et al. |
| 2012/0310064 A1 | 12/2012 | Mcgee |
| 2013/0006238 A1 | 1/2013 | Ditter et al. |
| 2013/0085361 A1 | 4/2013 | Mercanzini et al. |
| 2013/0096432 A1 | 4/2013 | Hauck |
| 2013/0158537 A1 | 6/2013 | Deladi et al. |
| 2013/0165916 A1 | 6/2013 | Mathur |
| 2013/0172715 A1 | 7/2013 | Just et al. |

(56) References Cited

U.S. PATENT DOCUMENTS

| | | |
|---|---|---|
| 2013/0190587 A1 | 7/2013 | Lopes et al. |
| 2013/0197614 A1 | 8/2013 | Gustus et al. |
| 2013/0225983 A1 | 8/2013 | Willis et al. |
| 2013/0226017 A1 | 8/2013 | Scharf et al. |
| 2013/0241929 A1 | 9/2013 | Massarwa et al. |
| 2013/0245433 A1 | 9/2013 | Deladi et al. |
| 2013/0245621 A1 | 9/2013 | Persson et al. |
| 2013/0253298 A1 | 9/2013 | Harlev et al. |
| 2013/0267853 A1 | 10/2013 | Dausch et al. |
| 2013/0274582 A1 | 10/2013 | Afonso et al. |
| 2013/0282084 A1 | 10/2013 | Mathur et al. |
| 2013/0304062 A1 | 11/2013 | Chan et al. |
| 2013/0304065 A1 | 11/2013 | Lopes et al. |
| 2013/0310827 A1 | 11/2013 | Brewster et al. |
| 2013/0330701 A1 | 12/2013 | Rubinstein et al. |
| 2014/0024910 A1 | 1/2014 | Scharf et al. |
| 2014/0095105 A1 | 4/2014 | Koyrakh et al. |
| 2014/0121470 A1 | 5/2014 | Scharf et al. |
| 2014/0148677 A1 | 5/2014 | Liempde et al. |
| 2014/0180150 A1 | 6/2014 | Scharf |
| 2014/0221803 A1 | 8/2014 | Bar-Tal et al. |
| 2014/0235988 A1 | 8/2014 | Ghosh |
| 2014/0249505 A1 | 9/2014 | Bukhman |
| 2014/0257069 A1 | 9/2014 | Eliason et al. |
| 2014/0257071 A1 | 9/2014 | Curran et al. |
| 2014/0275921 A1 | 9/2014 | Harlev et al. |
| 2014/0276733 A1 | 9/2014 | VanScoy et al. |
| 2014/0276746 A1 | 9/2014 | Nabutovsky et al. |
| 2014/0276789 A1 | 9/2014 | Dandler et al. |
| 2014/0278129 A1* | 9/2014 | Voth .................... A61B 5/287 702/19 |
| 2014/0358143 A1 | 12/2014 | Novichenok et al. |
| 2015/0038862 A1 | 2/2015 | Gijsbers et al. |
| 2015/0196217 A1 | 7/2015 | Harlev et al. |
| 2015/0196219 A1 | 7/2015 | Scharf et al. |
| 2015/0208938 A1 | 7/2015 | Houben et al. |
| 2015/0223757 A1 | 8/2015 | Werneth et al. |
| 2015/0223863 A1 | 8/2015 | Ghosh |
| 2015/0257732 A1 | 9/2015 | Ryan |
| 2015/0257825 A1 | 9/2015 | Kelly et al. |
| 2015/0294082 A1 | 10/2015 | Passerini et al. |
| 2015/0342491 A1 | 12/2015 | Marecki et al. |
| 2015/0366508 A1 | 12/2015 | Chou et al. |
| 2015/0374252 A1 | 12/2015 | de la Rama et al. |
| 2016/0007869 A1 | 1/2016 | Scharf et al. |
| 2016/0038051 A1 | 2/2016 | Scharf et al. |
| 2016/0051321 A1 | 2/2016 | Salahieh et al. |
| 2016/0100770 A1 | 4/2016 | Afonso et al. |
| 2016/0128771 A1 | 5/2016 | Ditter et al. |
| 2016/0128772 A1 | 5/2016 | Reinders et al. |
| 2016/0192902 A1 | 7/2016 | Werneth et al. |
| 2016/0256112 A1 | 9/2016 | Brockway et al. |
| 2017/0035486 A1 | 2/2017 | Lopes et al. |
| 2017/0065204 A1 | 3/2017 | Ludwin et al. |
| 2017/0100049 A1 | 4/2017 | Scharf et al. |
| 2017/0202469 A1 | 7/2017 | Scharf et al. |
| 2017/0258347 A1 | 9/2017 | Scharf et al. |
| 2017/0319180 A1 | 11/2017 | Henneken et al. |
| 2018/0055374 A1 | 3/2018 | Scharf et al. |
| 2018/0146948 A1 | 5/2018 | Chou et al. |
| 2018/0296114 A1 | 10/2018 | Welsh et al. |
| 2018/0315347 A1 | 11/2018 | Zhu et al. |
| 2019/0159729 A1 | 5/2019 | Chou et al. |
| 2019/0200886 A1* | 7/2019 | Welsh .................... A61B 5/291 |
| 2020/0138317 A1 | 5/2020 | Scharf et al. |
| 2020/0187801 A1 | 6/2020 | Scharf et al. |
| 2021/0068694 A1 | 3/2021 | Chou et al. |
| 2022/0095980 A1 | 3/2022 | Scharf et al. |

FOREIGN PATENT DOCUMENTS

| | | |
|---|---|---|
| CN | 1856213 | 11/2006 |
| CN | 101048100 | 10/2007 |
| CN | 201223445 | 4/2009 |
| CN | 201275144 | 7/2009 |
| CN | 102770085 | 11/2012 |
| CN | 104462650 | 3/2015 |
| CN | 105025783 | 11/2015 |
| EP | 1166714 | 1/2002 |
| EP | 1415608 | 10/2004 |
| EP | 1760661 | 3/2007 |
| EP | 1779787 | 5/2007 |
| EP | 2051625 | 4/2009 |
| EP | 2252203 | 11/2010 |
| EP | 2683293 | 1/2014 |
| EP | 2953550 | 8/2016 |
| JP | 08501477 | 2/1996 |
| JP | 08504333 | 5/1996 |
| JP | 08164140 | 6/1996 |
| JP | 10137207 | 5/1998 |
| JP | 11504541 | 4/1999 |
| JP | 2000510030 | 8/2000 |
| JP | 2000510250 | 8/2000 |
| JP | 2000358299 | 12/2000 |
| JP | 2001070269 | 3/2001 |
| JP | 2001522288 | 11/2001 |
| JP | 2002051998 | 2/2002 |
| JP | 2002113004 | 4/2002 |
| JP | 2002522106 | 7/2002 |
| JP | 2003509145 | 3/2003 |
| JP | 2003511098 | 3/2003 |
| JP | 2004350702 | 12/2004 |
| JP | 2005536313 | 12/2005 |
| JP | 2006511296 | 4/2006 |
| JP | 2006525072 | 11/2006 |
| JP | 2008149132 | 7/2008 |
| JP | 2009135109 | 6/2009 |
| JP | 2009136679 | 6/2009 |
| JP | 2011504363 | 2/2011 |
| JP | 2011507656 | 3/2011 |
| JP | 2012509701 | 4/2012 |
| JP | 2013188476 | 9/2013 |
| JP | 2014506171 | 3/2014 |
| JP | 2014514031 | 6/2014 |
| JP | 2014516723 | 7/2014 |
| JP | 2016511026 | 4/2016 |
| JP | 2017514553 | 6/2017 |
| WO | 9406349 | 3/1994 |
| WO | 9905971 | 2/1999 |
| WO | 0040166 | 7/2000 |
| WO | 2006060613 | 6/2006 |
| WO | 2008014629 | 2/2008 |
| WO | 2009065042 | 5/2009 |
| WO | 2009090547 | 7/2009 |
| WO | 2011136867 | 11/2011 |
| WO | 2012122517 | 9/2012 |
| WO | 2014124231 | 2/2013 |
| WO | 2013101257 | 7/2013 |
| WO | 2013123549 | 8/2013 |
| WO | 2014036439 | 3/2014 |
| WO | 20014059308 | 4/2014 |
| WO | 2014130169 | 8/2014 |
| WO | 2014137897 | 9/2014 |
| WO | 2015038607 | 3/2015 |
| WO | 2015148470 | 10/2015 |
| WO | 2016183179 | 11/2016 |
| WO | 2016183285 | 11/2016 |
| WO | 2016183468 | 11/2016 |
| WO | 2017192769 | 11/2017 |
| WO | 2017192775 | 11/2017 |
| WO | 2019144103 | 7/2019 |
| WO | 2019217430 | 11/2019 |
| WO | 2020097438 | 5/2020 |

OTHER PUBLICATIONS

Communication Under Rule 71(3) EPC dated Nov. 15, 2021 issued in corresponding European Application No. 15768711.2.
Extended European Search Report dated Dec. 13, 2021 issued in corresponding European Application No. 19800090.3.
Israel Office Action dated Dec. 5, 2023 issued in Israel Application No. 281160, with English translation.

(56) References Cited

OTHER PUBLICATIONS

International Search Report and Written Opinion dated Aug. 18, 2016 issued in corresponding International Application No. PCT/US16/32420.
International Search Report and Written Opinion dated Aug. 4, 2017 issued in corresponding International Application No. PCT/US17/30915.
International Search Report and Written Opinion dated Aug. 8, 2016 issued in corresponding European Application No. PCT/US2016/031823.
International Search Report and Written Opinion dated Dec. 12, 2017 issued in corresponding International Application No. PCT/US2017/056064.
International Search Report and Written Opinion dated Jan. 14, 2020 issued in International Application No. PCT/US2019/060433.
International Search Report and Written Opinion dated Jul. 21, 2020 issued in corresponding International Application No. PCT/US2020/028779.
International Search Report and Written Opinion dated Jul. 23, 2019 issued in corresponding International Application No. PCT/US2019/031131.
International Search Report and Written Opinion dated Jun. 26, 2015 issued in International Application No. PCT/US2015/022187.
International Search Report and Written Opinion dated Jun. 5, 2014 issued in corresponding International Application No. PCT/US2013/057579.
International Search Report and Written Opinion dated Mar. 10, 2015 issued in corresponding International Application No. PCT/US14/54942.
International Search Report and Written Opinion dated Mar. 5, 2013 issued in corresponding International Application No. PCT/US2012/028593.
International Search Report and Written Opinion dated May 20, 2014 issued in corresponding International Application No. PCT/US14/15261.
International Search Report and Written Opinion dated Sep. 14, 2020 issued in corresponding International Application No. PCT/US2020/036110.
International Search Report and Written Opinion dated Sep. 25, 2017, issued in corresponding Application No. PCT/US17/30922.
International Search Report dated Oct. 7, 2009 issued in corresponding International Application No. PCT/IB2009/000071.
International Search Report issued Apr. 21, 2008 in related International Application No. PCT/CH2007/000380.
Invitation to Pay Additional Fees issued on Jan. 8, 2014 in corresponding International Application No. PCT/US2013/057579.
Japanese Notice of Allowance dated Feb. 27, 2018 issued in corresponding Japanese Application No. 2015-530101.
Japanese Notice of Allowance dated Jul. 11, 2017 issued in corresponding Japanese Application No. 2013-557-926, with English language summary.
Japanese Notice of Allowance dated Jul. 7, 2020 issued in corresponding Japanese Application No. 2016558799, with English translation of allowed claims.
Japanese Notice of Allowance dated Jun. 11, 2019 issued in corresponding Japanese Application No. 2018-024907, with English translation.
Japanese Notice of Allowance dated Mar. 5, 2019 issued in corresponding Japanese Application No. 2018061040, with English translation.
Japanese Notice of Allowance dated Sep. 1, 2020 issued in corresponding Japanese Application No. 2017-559320, with English summary.
Japanese Notice of Allowance dated Sep. 18, 2018 issued in corresponding Japanese Application No. 2015-557091, with English language translation.
Japanese Office Action dated Aug. 28, 2018 issued in corresponding Japanese Application No. 2016-542062, with machine translation to English.
Japanese Office Action dated Dec. 11, 2018 issued in corresponding Japanese Application No. 2018-024907, with machine translation to English.
Japanese Office Action dated Feb. 16, 2016 issued in corresponding Japanese Application No. 2013-557-926, with English language summary.
Japanese Office Action dated Feb. 19, 2019 issued in corresponding Japanese Application No. 2016-558799, with machine translation to English.
Japanese Office Action dated Jan. 31, 2017 issued in corresponding Japanese Application No. 2013-557-926, with English language summary.
Japanese Office Action dated Jan. 7, 2020 issued in corresponding Japanese Application No. 2016-558799, with machine translation to English.
Japanese Office Action dated Jul. 23, 2019 issued in corresponding Japanese Application No. 2016-542062, with machine translation to English.
Japanese Office Action dated Jul. 28, 2020 issued in corresponding Japanese Application No. 2018-195960, with machine translation to English.
Japanese Office Action dated Jun. 27, 2017 issued in corresponding Japanese Application No. 2015-530101, with English language translation.
Japanese Office Action dated Jun. 30, 2020 issued in corresponding Japanese Application No. 2017559317, with machine translation to English.
Japanese Office Action dated Mar. 10, 2020 issued in corresponding Japanese Application No. 2017-559320, with machine translation to English.
Japanese Office Action dated Mar. 17, 2020 issued in corresponding Japanese Application No. 2019-071004, with machine translation to English.
Japanese Office Action dated Oct. 10, 2017 issued in corresponding Japanese Application No. 2015-557091, with machine translation to English.
Japanese Office Action dated Oct. 15, 2019 issued in corresponding Japanese Application No. 2018-195960, with machine translation to English.
Japanese Office Action dated Sep. 26, 2017 issued in corresponding Japanese Application No. 2017-155346, with English translation.
Summons To Attend Oral Proceedings dated Dec. 20, 2019 issued in corresponding European Application No. 13763151.1.
Della Bella et al. "Non-contact mapping to guide catheter ablation of untolerated ventrical tachycardia" European Heart Journal, May 2002, 23(9)742-752.
Gupta et al. "Point of View Cardiac Mapping: Utility or Futility?", Indian Pacing and Electrophysiology Journal, vol. 2, No. 1, 2002, pp. 20-32.
He et al. "An equivalent body surface charge model representing three-dimensional bioelectrical activity" IEEE Transactions on Biomedical Engineering, 42.7 (Jul. 7, 1995) pp. 637-646.
Jackson, JD, "Surface Distributions of Charges and Dipoles and Discontinuities in the Electric Field and Potential", Classical Electrodynamics, 3rd edition, Dec. 1998, pp. 31-34.
Leif et al., "Geometric modeling based on polygonal meshes". Eurographics 2000 Tutorial, Aug. 21, 2000.
Partial European Search Report dated Apr. 29, 2014 issued in corresponding European Application No. 13176658.
Pullan et al. "The inverse problem of electrocardiology" Northeastern University Electrical and Computer Engineering, Feb. 23, 2007.
Stevenson et al. "Recording Techniques for Clinical Electrophysiology", Journal of Cardiovascular Electrophysiology, vol. 16, No. 9, Sep. 2005, pp. 1017-1022.
Van Oosterom A: "Solidifying the solid angle." 2002 Journal of Electrocardiology 2002 vol. 35 Suppl pp. 181-192 ISSN: 0022-0736.
Wolfgang Nolting: Elektrodynamik—Grundkurs Theoretische Physik 3, Springer Spectrum, p. 89-91.
Japanese Office Action dated Nov. 2, 2021 issued in corresponding Japanese Application No. 2020-192741, with English translation.
Extended European Search Report dated Jul. 23, 2021 issued in corresponding European Application No. 21150862.7.

(56) References Cited

OTHER PUBLICATIONS

Anatomy Warehouse, "Axis Heart Model", 2014, pp. 1-3, at http://www.anatomywarehouse.com/axis-scientific-2-part-deluxe-life-size-human-heart-a-104269. (Year: 2014).
Christoph Scharf et al. Declaration under 37 C.F.R. 1.132, Nov. 15, 2012.
Australian Examination Report dated Feb. 8, 2019 issued in corresponding Australian Application No. 2018250516.
Australian Examination Report dated Jun. 28, 2018 issued in corresponding Australian Patent Application No. 2014318872.
Australian Office Action dated Dec. 22, 2019 issued in corresponding Australian Application No. 2018278959.
Australian Office Action dated Feb. 26, 2018 issued in Australian Application No. 2017201560.
Australian Office Action dated Jan. 15, 2020 issued in corresponding Australian Application No. 2016262547.
Australian Office Action dated Jan. 26, 2019 issued in corresponding Australian Application No. 2018211348.
Australian Office Action dated Jul. 6, 2017 issued in corresponding Australian Application No. 2014214756.
Australian Office Action dated Jun. 14, 2018 issued in Australian Application No. 2014214756.
Australian Office Action dated Jun. 27, 2017 issued in corresponding Australian Application No. 2013308531.
Australian Office Action dated Mar. 16, 2020 issued in corresponding Australian Application No. 2016260522.
Australian Office Action dated Mar. 17, 2018 issued in corresponding Australian Application No. 2013308531.
Australian Office Action dated May 30, 2016 issued in related Australian Application No. 2012225250.
Australian Office Action dated Sep. 21, 2016 issued in corresponding Australian Application No. 2012225250.
Canadian Office Action dated Apr. 26, 2017 issued in corresponding Canadian Application No. 2932956.
Canadian Office Action dated Apr. 27, 2016 issued in corresponding Canadian Application No. 2747859.
Canadian Office Action dated Dec. 22 2015 issued in corresponding Canadian Application No. 2656898.
Canadian Office Action dated Jan. 22, 2018 issued in corresponding Canadian Application No. 2932956.
Canadian Office Action dated Jul. 12, 2019 issued in corresponding Canadian Application No. 2881457.
Canadian Office Action dated Mar. 30, 2017 issued in corresponding Canadian Application No. 2747859.
Canadian Office Action dated May 20, 2020 issued in corresponding Canadian Application No. 2881457.
Canadian Office Action dated Nov. 27, 2017 issued in corresponding Canadian Application No. 2829626.
Canadian Office Action dated Nov. 7, 2018 issued in corresponding Canadian Application No. 2932956.
Canadian Office Action dated Oct. 29, 2018 issued in corresponding Canadian Application No. 2829626.
Canadian Office Action dated Oct. 4, 2013 issued in corresponding Canadian Application No. 2659898.
Chinese Office Action dated Apr. 17, 2017 issued in corresponding Chinese Application No. 201480018328.4.
Chinese Office Action dated Apr. 8, 2020 issued in corresponding Chinese Application No. 201810153436.2.
Decision dated Jan. 16, 2018 issued for European Patent Application No. 09702094.5.
Decision dated Jan. 18, 2018 issued for European Patent Application No. 13176658.6.
European Office Action dated Apr. 23, 2018 issued in corresponding European Application No. 07785075.8.
European Office Action dated Apr. 28, 2014 issued in corresponding European Application No. 09702094.5.
European Office Action dated Feb. 29, 2016 issued in corresponding European Application No. 07785075.8.
European Office Action dated Feb. 6, 2019 issued in corresponding European Application No. 14843283.4.
European Office Action dated Jan. 28, 2019 issued in corresponding European Application No. 14748567.6.
European Office Action dated Jan. 31, 2018 issued in corresponding European Application No. 13763151.1.
European Office Action dated Jun. 15, 2020 issued in corresponding European Application No. 15768711.2.
European Office Action dated Mar. 21, 2017 issued in corresponding European Application No. 07785075.8.
European Office Action dated Mar. 9, 2016 issued in corresponding European Application No. 09702094.5.
European Office Action dated Mar. 9, 2016 issued in corresponding European Application No. 13176658.6.
European Office Action dated Nov. 7, 2017 issued in corresponding European Application No. 15768711.
Extended European Search Report dated Dec. 5, 2018 issued in corresponding European Application No. 16793622.8.
Extended European Search Report dated Jul. 8, 2016 issued in corresponding European Application No. 14748567.6.
Extended European Search Report dated Mar. 14, 2017 issued in corresponding European Application No: 14843283.4.
Extended European Search Report dated Nov. 26, 2019 issued in corresponding European Application No. 19184148.5.
Extended European Search Report dated Oct. 18, 2017 issued in European Application No. 15768711.
Extended European Search Report dated Oct. 4, 2018 issued in corresponding European Application No. 16793503.0.
Extended European Search Report dated Sep. 29, 2014 issued in corresponding European Application No. 13176658.
International Search Report and Written Opinion dated Apr. 8, 2019, issued in corresponding International Application No. PCT/US19/14498.
International Search Report and Written Opinion dated Aug. 11, 2016 issued in corresponding International Application No. PCT/US2016/032017.
Extended European Search Report dated Aug. 10, 2021 issued in corresponding European Application No. 19741310.7.
Flavia et al. "Wave Similarity Mapping Shows the Spatiotemporal Distribution of Fibrillatory Wave Complexity in the Human Right Atrium During Paroxysmal and Chronic Atrial Fibrillation", Journal of Cardiovascular Electrophysiology, vol. 16, No. 10 (Oct. 2005) pp. 1071-1076.
Japanese Office Action dated Jun. 29, 2021 issued in corresponding Japanese Application No. 2020-081074, with machine translation to English.
Chinese Office Action dated Jun. 22, 2024 issued in Chinese Application No. 201980067430.6, with machine translation to English.
Australian Office Action dated Jul. 5, 2024 issued in Australian Application No. 2019377121.

* cited by examiner

SYSTEMS AND METHODS FOR CALCULATING PATIENT INFORMATION

RELATED APPLICATIONS

The present application claims priority to U.S. Provisional Patent Application Ser. No. 62/757,961, entitled "Systems and Methods for Calculating Patient Information", filed Nov. 9, 2018, which is hereby incorporated by reference.

The present application, while not claiming priority to, may be related to U.S. application Ser. No. 16/335,893, entitled "Ablation System with Force Control", filed Mar. 22, 2019, which is a 35 USC 371 national stage filing of Patent Cooperation Treaty Application No. PCT/US2017/056064, entitled "Ablation System with Force Control", filed Oct. 11, 2017, published as WO2018/071490, which claims priority to U.S. Provisional Application Ser. No. 62/406,748, entitled "Ablation System with Force Control", filed Oct. 11, 2016, and U.S. Provisional Application Ser. No. 62/504,139, entitled "Ablation System with Force Control", filed May 20, 2017, each of which is hereby incorporated by reference.

The present application, while not claiming priority to, may be related to U.S. application Ser. No. 16/097,955, entitled "Cardiac Information Dynamic Display System and Method", filed Oct. 31, 2018, which is a 35 USC 371 national stage filing of Patent Cooperation Treaty Application No. PCT/US2017/030915, entitled "Cardiac Information Dynamic Display System and Method", filed May 3, 2017, published as WO 2017/192769, which claims priority to U.S. Provisional Application Ser. No. 62/331,351, entitled "Cardiac Information Dynamic Display System and Method", filed May 3, 2016, each of which is hereby incorporated by reference.

The present application, while not claiming priority to, may be related to U.S. application Ser. No. 16/012,051, entitled "Catheter, System and Methods of Medical Uses of Same, Including Diagnostic and Treatment Uses for the Heart", filed Jun. 19, 2018, which is a continuation of U.S. Pat. No. 10,004,459, entitled "Catheter, System and Methods of Medical Uses of Same, Including Diagnostic and Treatment Uses for the Heart", filed Feb. 20, 2015, which is a 35 USC 371 national stage filing of Patent Cooperation Treaty Application No. PCT/US2013/057579, entitled "Catheter System and Methods of Medical Uses of Same, Including Diagnostic and Treatment Uses for the Heart", filed Aug. 30, 2013, published as WO 2014/036439, which claims priority to U.S. Patent Provisional Application Ser. No. 61/695,535, entitled "System and Method for Diagnosing and Treating Heart Tissue", filed Aug. 31, 2012, each of which is hereby incorporated by reference.

The present application, while not claiming priority to, may be related to U.S. patent application Ser. No. 16/242,810, entitled "Expandable Catheter Assembly with Flexible Printed Circuit Board (PCB) Electrical Pathways", filed Jan. 8, 2019, which is a continuation of U.S. patent application Ser. No. 14/762,944, entitled "Expandable Catheter Assembly with Flexible Printed Circuit Board (PCB) Electrical Pathways", filed Jul. 23, 2015, which is a 35 USC 371 national stage filing of Patent Cooperation Treaty Application No. PCT/US2014/015261, entitled "Expandable Catheter Assembly with Flexible Printed Circuit Board (PCB) Electrical Pathways", filed Feb. 7, 2014, published as WO 2014/124231, which claims priority to U.S. Patent Provisional Application Ser. No. 61/762,363, entitled "Expandable Catheter Assembly with Flexible Printed Circuit Board (PCB) Electrical Pathways", filed Feb. 8, 2013, each of which is hereby incorporated by reference.

The present application, while not claiming priority to, may be related to U.S. patent application Ser. No. 16/533,028, entitled "Method and Device for Determining and Presenting Surface Charge and Dipole Densities on Cardiac Walls", filed Aug. 6, 2019, which is a continuation of U.S. patent application Ser. No. 16/014,370, entitled "Method and Device for Determining and Presenting Surface Charge and Dipole Densities on Cardiac Walls", filed Jun. 21, 2018, which is a continuation of U.S. patent application Ser. No. 15/435,763, entitled "Method and Device for Determining and Presenting Surface Charge and Dipole Densities on Cardiac Walls", filed Feb. 17, 2017, which is a continuation of U.S. Pat. No. 9,610,024, entitled "Method and Device for Determining and Presenting Surface Charge and Dipole Densities on Cardiac Walls", filed Sep. 25, 2015, which is a continuation of U.S. Pat. No. 9,167,982, entitled "Method and Device for Determining and Presenting Surface Charge and Dipole Densities on Cardiac Walls", filed Nov. 19, 2014, which is a continuation of U.S. Pat. No. 8,918,158 (hereinafter the '158 patent), entitled "Method and Device for Determining and Presenting Surface Charge and Dipole Densities on Cardiac Walls", issued Dec. 23, 2014, which is a continuation of U.S. Pat. No. 8,700,119 (hereinafter the '119 patent), entitled "Method and Device for Determining and Presenting Surface Charge and Dipole Densities on Cardiac Walls", issued Apr. 15, 2014, which is a continuation of U.S. Pat. No. 8,417,313 (hereinafter the '313 patent), entitled "Method and Device for Determining and Presenting Surface Charge and Dipole Densities on Cardiac Walls", issued Apr. 9, 2013, which was a 35 USC 371 national stage filing of PCT Application No. PCT/CH2007/000380, entitled "Method and Device for Determining and Presenting Surface Charge and Dipole Densities on Cardiac Walls", filed Aug. 3, 2007, published as WO 2008/014629, which claimed priority to Swiss Patent Application No. 1251/06 filed Aug. 3, 2006, each of which is hereby incorporated by reference.

The present application, while not claiming priority to, may be related to U.S. patent application Ser. No. 16/568,768, entitled "Device and Method for the Geometric Determination of Electrical Dipole Densities on the Cardiac Wall", filed Sep. 12, 2019, which is a continuation of U.S. patent application Ser. No. 15/882,097, entitled "Device and Method for the Geometric Determination of Electrical Dipole Densities on the Cardiac Wall", filed Jan. 29, 2018, which is a continuation of U.S. Pat. No. 9,913,589, entitled "Device and Method for the Geometric Determination of Electrical Dipole Densities on the Cardiac Wall", filed Dec. 25, 2016, which is a continuation of U.S. Pat. No. 9,504,395, entitled "Device and Method for the Geometric Determination of Electrical Dipole Densities on the Cardiac Wall", filed Oct. 19, 2015, which is a continuation of U.S. Pat. No. 9,192,318, entitled "Device and Method for the Geometric Determination of Electrical Dipole Densities on the Cardiac Wall", filed Jul. 19, 2013, which is a continuation of U.S. Pat. No. 8,512,255, entitled "Device and Method for the Geometric Determination of Electrical Dipole Densities on the Cardiac Wall", issued Aug. 20, 2013, published as US2010/0298690 (hereinafter the '690 publication), which was a 35 USC 371 national stage application of Patent Cooperation Treaty Application No. PCT/IB2009/000071 filed Jan. 16, 2009, entitled "A Device and Method for the Geometric Determination of Electrical Dipole Densities on the Cardiac Wall", published as WO2009/090547, which claimed priority to Swiss Patent Application 00068/08 filed Jan. 17, 2008, each of which is hereby incorporated by reference.

The present application, while not claiming priority to, may be related to U.S. patent application Ser. No. 16/389, 006, entitled "Device and Method for the Geometric Determination of Electrical Dipole Densities on the Cardiac Wall", filed Apr. 19, 2019, which is a continuation of U.S. application Ser. No. 15/926,187, entitled "Device and Method for the Geometric Determination of Electrical Dipole Densities on the Cardiac Wall", filed Mar. 20, 2018, which is a continuation of U.S. Pat. No. 9,968,268, entitled "Device and Method for the Geometric Determination of Electrical Dipole Densities on the Cardiac Wall", filed Aug. 8, 2017, which is a continuation of U.S. Pat. No. 9,757,044, entitled "Device and Method for the Geometric Determination of Electrical Dipole Densities on the Cardiac Wall", filed Sep. 6, 2013, which is a 35 USC 371 national stage filing of Patent Cooperation Treaty Application No. PCT/US2012/028593, entitled "Device and Method for the Geometric Determination of Electrical Dipole Densities on the Cardiac Wall", published as WO2012/122517 (hereinafter the '517 publication), which claimed priority to U.S. Patent Provisional Application Ser. No. 61/451,357, each of which is hereby incorporated by reference.

The present application, while not claiming priority to, may be related to U.S. Design patent application Ser. No. 29/681,827, entitled "Set of Transducer-Electrode Pairs for a Catheter", filed Feb. 28, 2019, which is a divisional of U.S. Design patent application Ser. No. 29/593,043, entitled "Set of Transducer-Electrode Pairs for a Catheter", filed Feb. 6, 2017, which is a divisional of US Design Pat. No. D782,686, entitled "Transducer-Electrode Pair for a Catheter", filed Dec. 2, 2013, which is a 35 USC 371 national stage filing of Patent Cooperation Treaty Application No. PCT/US2013/057579, entitled "Catheter System and Methods of Medical Uses of Same, Including Diagnostic and Treatment Uses for the Heart", filed Aug. 30, 2013, which claims priority to U.S. Patent Provisional Application Ser. No. 61/695,535, entitled "System and Method for Diagnosing and Treating Heart Tissue", filed Aug. 31, 2012, each of which is hereby incorporated by reference.

The present application, while not claiming priority to, may be related to U.S. patent application Ser. No. 16/111,538, entitled "Gas-Elimination Patient Access Device", filed Aug. 24, 2018, which is a continuation of U.S. Pat. No. 10,071,227, entitled "Gas-Elimination Patient Access Device", filed Jul. 14, 2016, which is a 35 USC 371 national stage filing of Patent Cooperation Treaty Application No. PCT/US2015/11312, entitled "Gas-Elimination Patient Access Device", filed Jan. 14, 2015, which claims priority to U.S. Patent Provisional Application Ser. No. 61/928,704, entitled "Gas-Elimination Patient Access Device", filed Jan. 17, 2014, which is hereby incorporated by reference.

The present application, while not claiming priority to, may be related to U.S. patent application Ser. No. 15/128, 563, entitled "Cardiac Analysis User Interface System and Method", filed Sep. 23, 2016, which is a 35 USC 371 national stage filing of Patent Cooperation Treaty Application No. PCT/US2015/22187, entitled "Cardiac Analysis User Interface System and Method", filed Mar. 24, 2015, which claims priority to U.S. Patent Provisional Application Ser. No. 61/970,027, entitled "Cardiac Analysis User Interface System and Method", filed Mar. 28, 2014, which is hereby incorporated by reference.

The present application, while not claiming priority to, may be related to U.S. patent application Ser. No. 14/916, 056, entitled "Devices and Methods for Determination of Electrical Dipole Densities on a Cardiac Surface", filed Mar. 2, 2016, which is a 35 USC 371 national stage filing of Patent Cooperation Treaty Application No. PCT/US2014/54942, entitled "Devices and Methods for Determination of Electrical Dipole Densities on a Cardiac Surface", filed Sep. 10, 2014, which claims priority to U.S. Patent Provisional Application Ser. No. 61/877,617, entitled "Devices and Methods for Determination of Electrical Dipole Densities on a Cardiac Surface", filed Sep. 13, 2013, which is hereby incorporated by reference.

The present application, while not claiming priority to, may be related to U.S. patent application Ser. No. 15/569, 457, entitled "Localization System and Method Useful in the Acquisition and Analysis of Cardiac Information", filed Oct. 26, 2017, which is a 35 USC 371 national stage filing of Patent Cooperation Treaty Application No. PCT/US2016/032420, entitled "Localization System and Method Useful in the Acquisition and Analysis of Cardiac Information", filed May 13, 2016, which claims priority to U.S. Patent Provisional Application Ser. No. 62/161,213, entitled "Localization System and Method Useful in the Acquisition and Analysis of Cardiac Information", filed May 13, 2015, which is hereby incorporated by reference.

The present application, while not claiming priority to, may be related to U.S. patent application Ser. No. 15/569, 231, entitled "Cardiac Virtualization Test Tank and Testing System and Method", filed Oct. 25, 2017, which is a 35 USC 371 national stage filing of Patent Cooperation Treaty Application No. PCT/US2016/031823, filed May 11, 2016, which claims priority to U.S. Patent Provisional Application Ser. No. 62/160,501, entitled "Cardiac Virtualization Test Tank and Testing System and Method", filed May 12, 2015, which is hereby incorporated by reference.

The present application, while not claiming priority to, may be related to U.S. patent application Ser. No. 15/569, 185, entitled "Cardiac Virtualization Test Tank and Testing System and Method", filed Oct. 25, 2017, which is a 35 USC 371 national stage filing of Patent Cooperation Treaty Application No. PCT/US2016/032017, filed May 12, 2016, which claims priority to U.S. Patent Provisional Application Ser. No. 62/160,529, entitled "Ultrasound Sequencing System and Method", filed May 12, 2015, which is hereby incorporated by reference.

The present application, while not claiming priority to, may be related to U.S. patent application Ser. No. 16/097, 959, entitled "Cardiac Mapping System with Efficiency Algorithm", filed Oct. 31, 2018, which is a 35 USC 371 national stage filing of Patent Cooperation Treaty Application No. PCT/US2017/030922, entitled "Cardiac Mapping System with Efficiency Algorithm", filed May 3, 2017, which claims priority to U.S. Patent Provisional Application Ser. No. 62/413,104, entitled "Cardiac Mapping System with Efficiency Algorithm", filed Oct. 26, 2016, which is hereby incorporated by reference.

The present application, while not claiming priority to, may be related to Patent Cooperation Treaty Application No. PCT/US2019/014498, entitled "System for Identifying Cardiac Conduction Patterns", filed Jan. 22, 2019, which claims priority to U.S. Patent Provisional Application Ser. No. 62/619,897, entitled "System for Recognizing Cardiac Conduction Patterns", filed Jan. 21, 2018, and U.S. Patent Provisional Application Ser. No. 62/668,647, entitled "System for Identifying Cardiac Conduction Patterns", filed May 8, 2018, each of which is hereby incorporated by reference.

The present application, while not claiming priority to, may be related to Patent Cooperation Treaty Application No.

PCT/US2019/031131, entitled "Cardiac Information Processing System", filed May 7, 2019, which claims priority to U.S. Provisional Application Ser. No. 62/668,659, entitled "Cardiac Information Processing System", filed May 8, 2018, and U.S. Patent Provisional Application Ser. No. 62/811,735, entitled "Cardiac Information Processing System", filed Feb. 28, 2019, each of which is hereby incorporated by reference.

The present application, while not claiming priority, may be related to U.S. Patent Provisional Application Ser. No. 62/835,538, entitled "System for Creating a Composite Map", filed Apr. 18, 2019, which is hereby incorporated by reference.

The present application, while not claiming priority, may be related to U.S. Patent Provisional Application Ser. No. 62/925,030, entitled "System for Creating a Composite Map", filed Oct. 23, 2019, which is hereby incorporated by reference.

FIELD OF THE INVENTION

The present invention relates generally to medical diagnostic and treatment systems, and in particular, systems which record physiologic data from a first location to provide patient information at a different location.

BACKGROUND

Systems used by a clinician to perform a medical procedure, such as a diagnostic and/or therapeutic procedure, usually require assessment of one or more patient parameters, such as electrical and/or mechanical properties of tissue, as well as other patient information useful in performing the medical procedure. Procedures in which tissue is treated (e.g. ablated) often include an assessment of untreated tissue (e.g. before treatment), partially treated tissue (e.g. during treatment), and/or treated tissue (e.g. after treatment). It is often difficult to perform the assessment at the treatment site, due to limited space and other reasons. Accuracy and specificity of available assessments can be limited, and lead to lack of safety and/or lack of effectiveness of the treatment.

There is a need for systems that provide tissue and other patient information in a safe, effective, reliable, and simplified manner.

SUMMARY

According to one aspect of the present inventive concepts, a method of calculating information of a patient, comprising: determining a transfer matrix; recording electric potentials via a first set of recording electrodes located at a first set of recording locations to create a first set of recorded signals; and calculating patient information for a set of target locations by applying the transfer matrix to the first set of recorded signals.

In some embodiments, the first set of recording electrodes comprises one or more electrodes.

In some embodiments, the first set of recording electrodes comprises two or more electrodes.

In some embodiments, the first set of recording electrodes comprises one or more electrodes selected from the group consisting of: body surface electrodes; intrabody electrodes; percutaneous electrodes; subcutaneous electrodes; and combinations thereof.

In some embodiments, the first set of recording electrodes comprises: at least one electrode positioned on the patient's skin; at least one electrode positioned on the endocardial surface of a heart chamber; and/or at least one electrode within a heart chamber offset from the endocardial wall of the heart chamber.

In some embodiments, the first set of electrodes comprises a set of electrodes configured to be positioned on the patient's skin, and comprises a material selected from the group consisting of: platinum iridium; gold; a polymer, such as a polymer coating; carbon; copper; silver-silver chloride; a conductive gel; and combinations thereof.

In some embodiments, the first set of electrodes comprises a set of electrodes configured to be positioned within the patient's body, and comprises a material selected from the group consisting of: platinum iridium; gold; a polymer, such as a polymer coating; carbon; and combinations thereof.

In some embodiments, the first set of recording electrodes comprises one, two, or more electrodes selected from the group consisting of: one or more electrodes configured to emit and/or receive a localization signal; multiple electrodes configured to produce an ECG signal, such as an ECG array of at least 9 or at least 12 electrodes; multiple electrodes configured to produce a high density ECGi signal; one or more electrodes configured to deliver cardiac pacing energy; one or more electrodes configured to deliver defibrillation energy; one or more electrodes configured to deliver therapeutic energy; and combinations thereof. The one, two, or more electrodes can be positioned on and/or within a patient garment. The patient garment can comprise a garment selected from the group consisting of: vest; shirt; strap; belt; and combinations thereof.

In some embodiments, the first set of recording electrodes are positioned on and/or within a patient garment. The patient garment can comprise a garment selected from the group consisting of: vest; shirt; strap; belt; and combinations thereof. The first set of recording electrodes can be positioned in a vertical arrangement, a horizontal arrangement, a diagonal arrangement, and/or a spiral arrangement relative to the patient. The first set of electrodes can be positioned on and/or within the patient garment in a defined pattern, and the pattern can define a coordinate system. The first set of electrodes can be configured to provide: arrhythmia monitoring; localization of devices positioned within the patient; and/or a map of electrical information of the patient's heart, such as voltage information, dipole density information, and/or surface charge information.

In some embodiments, the first set of recording locations comprise one or more locations on the skin of the patient. The first set of recording locations can comprise a location selected from the group consisting of: chest; back; torso; shoulder, abdomen; skull; face; arm; leg; groin; and combinations thereof. The set of target locations can further comprise one or more locations within the patient. The one or more locations within the patient can comprise locations proximate the patient's heart. The one or more locations within the patient can comprise one or more locations selected from the group consisting of: epicardial surface; within heart tissue; endocardial surface; within a heart chamber; pericardial cavity; pericardium; and combinations thereof.

In some embodiments, the first set of recording locations comprises one or more locations within the patient. The first set of recording locations can comprise one or more intrabody locations selected from the group consisting of: within a heart chamber; on an endocardial surface; on an epicardial surface; and combinations thereof. The first set of recording locations can comprise one or more intrabody locations selected from the group consisting of: esophagus; epicardium; pericardium; interstitial fluid and/or other tissue structures surrounding the heart; interstitial fluid and/or other tissue structures under the skin; subcutaneous tissue; spine tissue; brain tissue; and combinations thereof. The first set of recording locations can comprise one or more locations within and/or otherwise proximate the patient's heart. The first set of recording locations can comprise one or more locations selected from the group consisting of: epicardial surface; within heart tissue; endocardial surface; within a heart chamber; pericardial cavity; pericardium; and combinations thereof.

In some embodiments, the first set of recording locations comprises locations on the skin of the patient and locations within the patient. The system can be configured to multiplex sourcing and sinking between electrodes on the skin of the patient and recording electrodes within the patient.

In some embodiments, the calculated patient information comprises information selected from the group consisting of: electrical information; voltage information; surface charge information; tissue charge information; dipole density information; tissue density information; electrographic flow information; impedance information; phase information; and combinations thereof.

In some embodiments, the calculated patient information comprises tissue density information. The tissue density information can comprise information related to changes in tissue density over time. The change in tissue density over time can comprise changes caused by ablation of the tissue.

In some embodiments, the transfer matrix comprises a characterization of electrical properties of tissue between the first set of recording locations and the set of target locations.

In some embodiments, the determining the transfer matrix comprises: emitting a set of drive signals via a set of drive electrodes located at a set of drive locations; and recording the emitted drive signals via a second set of recording electrodes located at a second set of recording locations to create a second set of recorded signals. The transfer matrix can be determined by comparing the second set of recorded signals to the emitted set of drive signals. The set of drive electrodes can comprise one or more electrodes. The set of drive electrodes can comprise two or more electrodes. The two or more electrodes can be positioned at least 2 mm apart from each other. The set of drive electrodes can be positioned on and/or within a patient garment. The patient garment can comprise a garment selected from the group consisting of: vest; shirt; strap; belt; and combinations thereof. The set of drive locations can comprise locations within the patient. The set of drive locations can comprise a location selected from the group consisting of: within a chamber of the heart; endocardial surface; epicardial surface, pericardial cavity; esophagus; and combinations thereof. The set of drive locations can comprise a location inside the heart. The second set of recording locations can comprise locations on the skin of the patient. The set of drive locations can comprise locations on the skin of the patient. The set of drive locations can comprise skin locations selected from the group consisting of: chest; back; torso; shoulder; abdomen; thorax; and combinations thereof. The second set of recording locations can comprise locations within the patient. The second set of recording locations can comprise locations selected from the group consisting of: within a heart chamber; on an endocardial surface; on an epicardial surface; pericardium; esophagus; interstitial fluid and/or other tissue structures surrounding the heart; interstitial fluid and/or other tissue structures under the skin; subcutaneous tissue; spine tissue; brain tissue; and combinations thereof. The drive signals can comprise: a first drive signal from a first drive electrode at a first frequency; and a second drive signal from a second drive electrode at a second frequency. The first frequency and the second frequency can be different. The first drive signal and the second drive signal can be delivered simultaneously. The drive signals can comprise: a first drive signal from a first drive electrode at a first frequency; and a second drive signal from a second drive electrode at a second frequency. The first drive signal and the second drive signal can be delivered sequentially. The first frequency and the second frequency can be the same frequency. The transfer matrix can be determined using the magnitude and/or phase of the second set of recorded signals. The transfer matrix can comprise a numerical scale factor based on a comparison of the magnitude and/or phase of the second set of recorded signals to the magnitude and/or phase of the set of drive signals. The transfer matrix can be determined using the magnitude and phase of the second set of recorded signals. The emitting of the set of drive signals and the recording of the emitted drive signals can occur over at least one physiologic cycle of the patient. The physiologic cycle can comprise a cycle selected from the group consisting of: a cardiac cycle; a respiratory cycle; a pressure cycle; and combinations thereof. The transfer matrix can compensate for respiration of the patient. The transfer matrix can compensate for cardiac motion of the patient. The transfer matrix can comprise a time-dependent transfer matrix including one or more components/factors that vary in unison with the physiologic cycle. The calculating of the calculated patient information can include aligning the time-dependent transfer matrix with the physiologic cycle. The transfer matrix can be proportionally adaptable over time. The determining the transfer matrix can further comprise incorporating information from a calculated and/or selected standardized transfer matrix.

In some embodiments, the determining of the transfer matrix comprises calculating and/or selecting a standardized transfer matrix. The standardized transfer matrix can be selected based on a patient parameter. The patient parameter can comprise a parameter selected from the group consisting of: gender; weight; height; body or body portion size; body mass index (BMI); thoracic cavity circumference; location of the esophagus; size of an atrium; filling of an atrial volume; atrial pressure; fat to water ratio; air to water to fat ratio; bone location; medications being taken; level of medication; electrolyte level; pH; pO2; pCO2; water weight; and combinations thereof.

In some embodiments, transfer matrix is modified over time. The transfer matrix can be modified based on at least one varying patient parameter. The at least one varying patient parameter can comprise at least two varying patient parameters, and the transfer matrix can be modified based on the at least two varying patient parameters. The varying patient parameter can comprise at least one cyclically varying patient parameter, and the transfer matrix can be modified based on the at least one cyclically varying patient parameter. The transfer matrix can be modified to compensate for respiration of the patient. The transfer matrix can be modified to compensate for cardiac motion of the patient. The method can further comprise monitoring the at least one varying patient parameter. The monitoring can comprise continuous monitoring of the at least one varying patient parameter. The transfer matrix can be modified continuously. The monitoring can comprise intermittent monitoring of the at least one varying patient parameter. The transfer matrix can be modified intermittently.

In some embodiments, the applying of the transfer matrix to the first set of recorded signals comprises applying a linear geometric function of the transfer matrix to the first set of recorded signals.

In some embodiments, the method further comprises gathering patient physiologic data. The patient physiologic data can comprise data selected from the group consisting of: physiologic cycle data; cardiac data; respiration data; patient medication data; skin impedance data; perspiration data; thoracic and/or abdominal cavity dimensional data; water weight data; hematocrit level data; wall thickness data; cardiac wall thickness data; and combinations thereof. The patient physiologic data can be gathered by at least one sensor. The patient physiologic data can be gathered by at least two sensors. The at least one sensor can comprise one, two, three or more sensors selected from the group consisting of: magnetic sensor; water sensor; perspiration sensor; skin impedance sensor; glucose sensor; pH sensor; pO2 sensor; pCO2 sensor; SpO2 sensor; heart rate sensor; pressure sensor; blood pressure sensor; spine sensor; brain electrode; brain sensor; flow sensor; blood flow sensor; movement sensor; and combinations thereof. The at least one sensor can be positioned on and/or within a patient garment. The patient garment can comprise a garment selected from the group consisting of: vest; shirt; strap; belt; and combinations thereof. The method can further comprise identifying changes to physiologic data over time and can modify the transfer matrix based on the identified changes.

In some embodiments, the method further comprises: recording voltages of the patient at an alpha location; and determining electrical information at a beta location. The beta location can be a different location than the alpha location. The determined electrical information can be based on the output of an inverse solution, and the transfer matrix can be applied to improve the quality of the determined electrical information. The transfer matrix can account for spatial anisotropy and/or temporal anisotropy.

In some embodiments, the method further comprises performing a device localization procedure to determine device location information. The transfer matrix can be applied to improve the quality of the determined device location information. The method can further comprise performing real-time updates of localization data.

The technology described herein, along with the attributes and attendant advantages thereof, will best be appreciated and understood in view of the following detailed description taken in conjunction with the accompanying drawings in which representative embodiments are described by way of example.

DETAILED DESCRIPTION OF THE DRAWINGS

Figure 1:
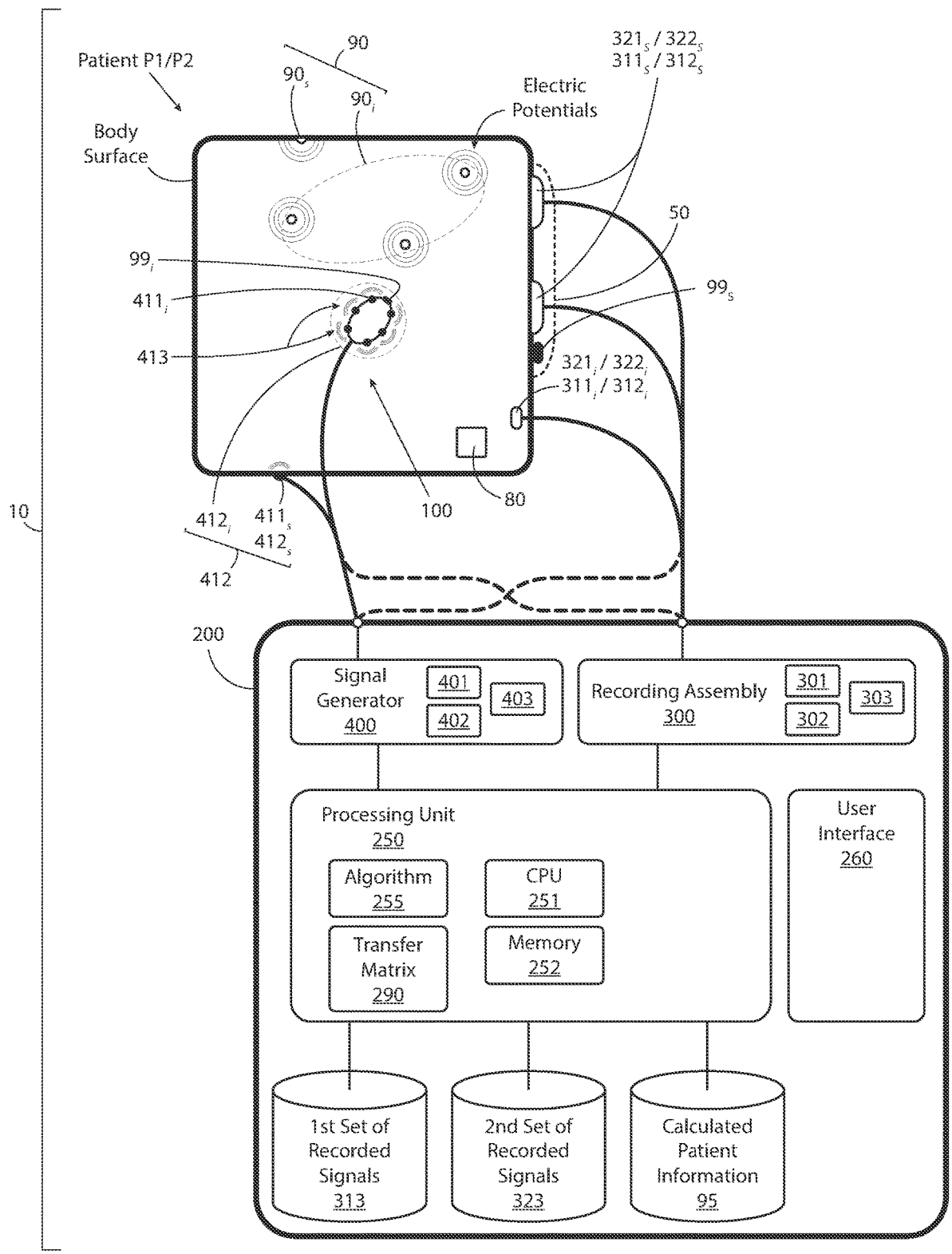
FIG. 1 illustrates a schematic view of a system for calculating information related to one or more parameters of a patient, consistent with the present inventive concepts.

Reference will now be made in detail to the present embodiments of the technology, examples of which are illustrated in the accompanying drawings. Similar reference numbers may be used to refer to similar components. However, the description is not intended to limit the present disclosure to particular embodiments, and it should be construed as including various modifications, equivalents, and/or alternatives of the embodiments described herein.

It will be understood that the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") when used herein, specify the presence of stated features, integers, steps, operations, elements, and/or components, but do not preclude the presence or addition of one or more other features, integers, steps, operations, elements, components, and/or groups thereof.

It will be further understood that, although the terms first, second, third, etc. may be used herein to describe various limitations, elements, components, regions, layers and/or sections, these limitations, elements, components, regions, layers and/or sections should not be limited by these terms. These terms are only used to distinguish one limitation, element, component, region, layer or section from another limitation, element, component, region, layer or section. Thus, a first limitation, element, component, region, layer or section discussed below could be termed a second limitation, element, component, region, layer or section without departing from the teachings of the present application.

It will be further understood that when an element is referred to as being "on", "attached", "connected" or "coupled" to another element, it can be directly on or above, or connected or coupled to, the other element, or one or more intervening elements can be present. In contrast, when an element is referred to as being "directly on", "directly attached", "directly connected" or "directly coupled" to another element, there are no intervening elements present. Other words used to describe the relationship between elements should be interpreted in a like fashion (e.g. "between" versus "directly between," "adjacent" versus "directly adjacent," etc.).

It will be further understood that when a first element is referred to as being "in", "on" and/or "within" a second element, the first element can be positioned: within an internal space of the second element, within a portion of the second element (e.g. within a wall of the second element); positioned on an external and/or internal surface of the second element; and combinations of one or more of these.

As used herein, the term "proximate", when used to describe proximity of a first component or location to a second component or location, is to be taken to include one or more locations near to the second component or location, as well as locations in, on and/or within the second component or location. For example, a component positioned proximate an anatomical site (e.g. a target tissue location), shall include components positioned near to the anatomical site, as well as components positioned in, on and/or within the anatomical site.

Spatially relative terms, such as "beneath," "below," "lower," "above," "upper" and the like may be used to describe an element and/or feature's relationship to another element(s) and/or feature(s) as, for example, illustrated in the figures. It will be further understood that the spatially relative terms are intended to encompass different orientations of the device in use and/or operation in addition to the orientation depicted in the figures. For example, if the device in a figure is turned over, elements described as "below" and/or "beneath" other elements or features would then be oriented "above" the other elements or features. The device can be otherwise oriented (e.g. rotated 90 degrees or at other orientations) and the spatially relative descriptors used herein interpreted accordingly.

The terms "reduce", "reducing", "reduction" and the like, where used herein, are to include a reduction in a quantity, including a reduction to zero. Reducing the likelihood of an occurrence shall include prevention of the occurrence. Correspondingly, the terms "prevent", "preventing", and "prevention" shall include the acts of "reduce", "reducing", and "reduction", respectively.

The term "and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

The term "one or more", where used herein can mean one, two, three, four, five, six, seven, eight, nine, ten, or more, up to any number.

The terms "and combinations thereof" and "and combinations of these" can each be used herein after a list of items that are to be included singly or collectively. For example, a component, process, and/or other item selected from the group consisting of: A; B; C; and combinations thereof, shall include a set of one or more components that comprise: one, two, three or more of item A; one, two, three or more of item B; and/or one, two, three, or more of item C.

In this specification, unless explicitly stated otherwise, "and" can mean "or", and "or" can mean "and". For example, if a feature is described as having A, B, or C, the feature can have A, B, and C, or any combination of A, B, and C. Similarly, if a feature is described as having A, B, and C, the feature can have only one or two of A, B, or C.

The expression "configured (or set) to" used in the present disclosure may be used interchangeably with, for example, the expressions "suitable for", "having the capacity to", "designed to", "adapted to", "made to" and "capable of" according to a situation. The expression "configured (or set) to" does not mean only "specifically designed to" in hardware. Alternatively, in some situations, the expression "a device configured to" may mean that the device "can" operate together with another device or component.

As used herein, the term "threshold" refers to a maximum level, a minimum level, and/or range of values correlating to a desired or undesired state. In some embodiments, a system parameter is maintained above a minimum threshold, below a maximum threshold, within a threshold range of values and/or outside a threshold range of values, to cause a desired effect (e.g. efficacious therapy) and/or to prevent or otherwise reduce (hereinafter "prevent") an undesired event (e.g. a device and/or clinical adverse event). In some embodiments, a system parameter is maintained above a first threshold (e.g. above a first temperature threshold to cause a desired therapeutic effect to tissue) and below a second threshold (e.g. below a second temperature threshold to prevent undesired tissue damage). In some embodiments, a threshold value is determined to include a safety margin, such as to account for patient variability, system variability, tolerances, and the like. As used herein, "exceeding a threshold" relates to a parameter going above a maximum threshold, below a minimum threshold, within a range of threshold values and/or outside of a range of threshold values.

The term "diameter" where used herein to describe a non-circular geometry is to be taken as the diameter of a hypothetical circle approximating the geometry being described. For example, when describing a cross section, such as the cross section of a component, the term "diameter" shall be taken to represent the diameter of a hypothetical circle with the same cross sectional area as the cross section of the component being described.

The terms "major axis" and "minor axis" of a component where used herein are the length and diameter, respectively, of the smallest volume hypothetical cylinder which can completely surround the component.

As used herein, the term "functional element" is to be taken to include one or more elements constructed and arranged to perform a function. A functional element can comprise a sensor and/or a transducer. In some embodiments, a functional element is configured to deliver energy and/or otherwise treat tissue (e.g. a functional element configured as a treatment element). Alternatively or additionally, a functional element (e.g. a functional element comprising a sensor) can be configured to record one or more parameters, such as a patient physiologic parameter; a patient anatomical parameter (e.g. a tissue geometry parameter); a patient environment parameter; and/or a system parameter. In some embodiments, a sensor or other functional element is configured to perform a diagnostic function (e.g. to gather data used to perform a diagnosis). In some embodiments, a functional element is configured to perform a therapeutic function (e.g. to deliver therapeutic energy and/or a therapeutic agent). In some embodiments, a functional element comprises one or more elements constructed and arranged to perform a function selected from the group consisting of: deliver energy; extract energy (e.g. to cool a component); deliver a drug or other agent; manipulate a system component or patient tissue; record or otherwise sense a parameter such as a patient physiologic parameter or a system parameter; and combinations of one or more of these. A "functional assembly" can comprise an assembly constructed and arranged to perform a function, such as a diagnostic and/or therapeutic function. A functional assembly can comprise an expandable assembly. A functional assembly can comprise one or more functional elements.

The term "transducer" where used herein is to be taken to include any component or combination of components that receives energy or any input and produces an output. For example, a transducer can include an electrode that receives electrical energy and distributes the electrical energy to tissue (e.g. based on the size of the electrode). In some configurations, a transducer converts an electrical signal into any output, such as light (e.g. a transducer comprising a light emitting diode or light bulb), sound (e.g. a transducer comprising a piezo crystal configured to deliver ultrasound energy), pressure, heat energy, cryogenic energy, chemical energy; mechanical energy (e.g. a transducer comprising a motor or a solenoid), magnetic energy, and/or a different electrical signal (e.g. a Bluetooth or other wireless communication element). Alternatively or additionally, a transducer can convert a physical quantity (e.g. variations in a physical quantity) into an electrical signal. A transducer can include any component that delivers energy and/or an agent to tissue, such as a transducer configured to deliver one or more of: electrical energy to tissue (e.g. a transducer comprising one or more electrodes); light energy to tissue (e.g. a transducer comprising a laser, light emitting diode and/or optical component such as a lens or prism); mechanical energy to tissue (e.g. a transducer comprising a tissue manipulating element); sound energy to tissue (e.g. a transducer comprising a piezo crystal); chemical energy; electromagnetic energy; magnetic energy; and combinations of one or more of these.

As used herein, the term "mapping procedure" shall include a clinical procedure performed on a patient that produces electrical activity information related to tissue of the patient, such as organ tissue (e.g. brain or heart tissue).

As used herein, the term "localization procedure" shall include the process of establishing a coordinate system, and using one or more signals, such as electrical signals, to determine the position of one or more objects or portions of objects ("objects" herein) within that system. In some embodiments, the process of localization incorporates one or more signals generated from one or more sources (e.g. electrodes), the signals changing as a function of space and/or time, and a sensor (e.g. an electrode) that measures the generated signals from a recording location. The recording location of the sensor can be on the object being localized or it can be separate from the object being localized. Analysis of and/or calculation performed on the measured signal can be used to determine a positional relationship of the sensor and/or the object to the one or more sources of the generated signal. The method of localization can incorporate two or more generated signals to increase the number or accuracy of positional relationships between the sensor and the signal source. The sensor and the object can be a single component and/or they can be multiple components that are co-located. In some embodiments, the signal change as a function of time and/or space includes interactions of the signal with the measurement environment. In other embodiments, the process of localization measures an intrinsic or existing characteristic of the object, sensor, or measurement environment, such as by measuring a signal from an accelerometer positioned on the object or sensor and incorporating information from the accelerometer signal in the analysis.

As used herein, the term "ablation procedure" shall include an ablative treatment procedure performed on patient tissue that has been identified as contributing to undesired electrical activity—such as activity associated with an arrhythmia of the heart (e.g. atrial fibrillation) or undesired state of the brain (e.g. seizure or tremor).

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination. For example, it will be appreciated that all features set out in any of the claims (whether independent or dependent) can be combined in any given way.

It is to be understood that at least some of the figures and descriptions of the invention have been simplified to focus on elements that are relevant for a clear understanding of the invention, while eliminating, for purposes of clarity, other elements that those of ordinary skill in the art will appreciate may also comprise a portion of the invention. However, because such elements are well known in the art, and because they do not necessarily facilitate a better understanding of the invention, a description of such elements is not provided herein.

Provided herein are systems and methods for calculating patient information. Patient physiologic data is recorded at one or more recording locations, and a transfer matrix is used to determine patient information at one or more target locations that can be remote from the recording locations. Electrical information can be recorded by electrodes placed on the skin of the patient and/or within the patient, and electrical and/or other patient information can be calculated at target locations, such as target locations including an organ of the patient (e.g. the heart or the brain). Systems of the present inventive concepts can include components used to determine the transfer matrix, such as electrodes or other sensors that characterize tissue properties between a recording location and a target location, the characterization performed on the patient for whom the patient information is to be calculated, and/or one or more similar mammalian subjects.

Referring now to FIG. 1, a schematic view of a system for calculating information related to one or more parameters of a patient is illustrated, consistent with the present inventive concepts. System 10 comprises recording assembly 300, which is configured to receive information from a set of one or more sensors, recording electrodes 311, each of which is placed at one or more associated recording locations 312 of a patient, such as patient P1 shown. System 10 can further comprise a console 200, including processing unit 250, which receives, via recording assembly 300, the signals produced by recording electrodes 311, and stores (e.g. in electronic memory 252) associated recorded signals 313. Processing unit 250 includes an algorithm 255 and transfer matrix 290. Processing unit 250 can be configured such that algorithm 255 applies transfer matrix 290 to convert the recorded signals 313 into calculated patient information 95, where information 95 represents patient physiologic parameter information at one or more patient locations 90 (e.g. one or more skin locations and/or one or more internal locations of the patient).

Transfer matrix 290 is a mathematical characterization of (all applicable) tissue, volume $V_X$, applicable to determining patient information 95 at one or more patient locations 90 based on recordings made at one or more recording locations 312. Recording locations 312 and a single patient location 90 define an intervening volume (e.g. volume of tissue and/or gas-filled space), volume $V_{I1}$, where volume $V_{I1}$ is defined by the space within a set of points (e.g. a convex hull) represented collectively by recording locations 312 and the patient location 90. Note that in some embodiments, one or more patient locations 90 lie within a tissue region or volume ("region" or "volume" herein) that is defined by recording locations 312 alone. Calculated patient information 95 at a single patient location 90 is highly dependent on the tissue and/or other material within volume $V_{I1}$. This calculated patient information 95 is also dependent (however less dependent) on a volume outside of the primary contributing volume $V_{I1}$, but proximate thereto, volume $V_{P1}$. The total contributing volume, volume $V_{T1}$, is defined by the primary contributing volume $V_{I1}$ combined with volume $V_{P1}$. Volume $V_X$ can comprise one or more volumes $V_{T1}$ (e.g. a volume $V_{T1}$ for each patient location 90), such that each volume $V_{T1}$ is a subset of Volume $V_X$.

Volume $V_X$ can comprise various forms of tissue (e.g. skin, subdermal tissue, blood vessel wall tissue, blood, heart, and/or other organ tissue, bone, and/or bone marrow), interstitial space, and/or open space (e.g. space within a patient's lung). Transfer matrix 290 can be configured to account for variations in tissue and/or other variations from one location to another location within volume $V_X$. Volume $V_X$ can comprise a time-varying volume, such as a volume that varies during a cardiac cycle (e.g. due to expansion and contraction of the heart and subsequent movement of surrounding tissue) and/or a respiratory cycle (e.g. due to expansion and contraction of the lungs and subsequent movement of surrounding tissue). Transfer matrix 290 can be configured to account for a time-varying volume of volume $V_X$. Volume $V_X$ can comprise tissue that has one or more tissue parameters, tissue parameter information 80 shown, that vary over time, such as: impedance (e.g. impedance changes due to respiration); pH; temperature; pO2; and/or pCO2 that varies over time. Transfer matrix 290 can be configured to account for temporal variations of these tissue parameters within volume $V_X$. In some embodiments, transfer matrix 290 compensates for electrode changes, such as transpiration of surface electrodes (e.g. polarization from electric current) and/or oxidation of electrodes (e.g. from blood reactant). In some embodiments, processing unit 250 stores one or more tissue parameter information 80 (e.g. for processing by algorithm 255).

In some embodiments, heart movement during systole can be determined by measuring changes of impedance between internal electrodes (e.g. one or more internal electrodes) and surface electrodes (e.g. one or more surface electrodes). This measured impedance change can represent the actual change in position, geometry, and/or other properties of the heart and it can be used to monitor heart function (e.g. tissue contractility, ejection fraction) during a clinical procedure, such as to monitor left ventricular volume over time.

In some embodiments, transfer matrix 290 is determined from information (e.g. electrical activity) recorded from patient P1, such as during a transfer matrix 290 creation procedure as described herebelow. Alternatively or additionally, transfer matrix 290 can be determined from information (e.g. electrical activity) recorded from a different patient, patient P2 (e.g. a different mammalian subject with similar physiologic attributes as patient P1), also as described herebelow.

In some embodiments, volume $V_X$ can comprise an intervening volume $V_{I2}$ defined by the space within a convex hull of a set of points represented by recording locations 312, and one or more drive locations (e.g. drive locations 412 described herebelow) from which drive signals (e.g. drive signals 413, also described herebelow) are emitted while transfer matrix 290 is determined. Transfer matrix 290 can be determined as described herebelow. In some embodiments, the convex hull of recording locations 312 encompasses each drive location 412, and volume $V_{I2}$ is defined by the convex hull of recording locations 312 alone. Transfer matrix 290 is primarily dependent on the tissue characteristics within volume $V_{I2}$. Volume $V_X$ can further comprise a volume $V_{P2}$ outside of the volume $V_{I1}$, but proximate thereto. Transfer matrix 290 is also dependent (however less dependent) on the tissue characteristics within volume $V_{P2}$. In some embodiments, a volume $V_{XP1}$ can be defined as described hereabove for a first patient P1, and a volume $V_{XP2}$ of a second patient P2 can approximate volume $V_{XP1}$ (e.g. approximate the size, shape, and physiologic characteristics of $V_{XP1}$).

In some embodiments, volume $V_X$ comprises an intervening volume $V_{I2}$ defined by the space between an arbitrary distribution of a set of points represented by recording locations 312, and the one or more drive locations 412 from which drive signals 413 are emitted while transfer matrix 290 is determined. Transfer matrix 290 can be determined as described herein. In some embodiments, the arbitrary distribution of recording locations 312 encompasses each drive location 412, and volume $V_{I2}$ is defined by the distribution of recording locations 312 alone. Transfer matrix 290 is primarily dependent on the tissue characteristics within volume $V_{I2}$. Volume $V_X$ can further comprise a volume $V_{P2}$ outside of the volume $V_{I1}$, but proximate the volume $V_{I1}$. Transfer matrix 290 is also dependent (however less dependent) on the tissue characteristics within volume $V_{P2}$. In some embodiments, a volume $V_{XP1}$ can be defined (e.g. as described hereabove) for a first patient P1, and a volume $V_{XP2}$ of a second patient P2 can approximate the volume $V_{XP1}$ (e.g. approximate the size, shape, and/or physiologic characteristics of $V_{XP1}$).

In some embodiments, console 200 or other component of system 10 includes an electronics assembly configured to deliver electrical energy (e.g. to deliver drive signals), signal generator 400 shown. In these embodiments, system 10 further comprises a set of one or more energy-delivering transducers, drive electrodes 411, which deliver drive signals 413 to tissue of a patient at one or more drive locations 412. Drive locations 412 can comprise one or more locations external to the patient location (e.g. on the skin of the patient), such as drive locations $412_s$ shown, and/or one or more locations within the patient (e.g. under the skin of the patient), drive locations $412_i$ shown. Drive signals 413 emitted by drive electrodes 411 can be used to determine and/or adjust ("determine" or "calculate" herein) transfer matrix 290 (e.g. as described herebelow), to perform a localization procedure (e.g. as described herebelow), to calibrate a localization coordinate system (e.g. an impedance field used to localize one or more devices positioned within the field), and/or to perform another function. Drive signals (e.g. drive signals 413) can comprise a signal selected from the group consisting of: a continuous wave; an impulse; a patterned sequence; an amplitude modulated signal; a frequency modulated signal; a chirp; and combinations thereof. In some embodiments, one or more drive signals (e.g. drive signals 413) are implemented based on electrical properties or other characteristics of the applicable tissue.

In some embodiments, system 10 comprises one or more patient insertable devices, such as device 100 shown. Device 100 can comprise a catheter or other patient insertable device, such as a device that includes drive electrodes 411 (as shown in FIG. 1).

In some embodiments, system 10 includes one or more patient-attachable garments or other patient-attachable components, garment 50 shown, which can be used to position one or more sensors of system 10 at one or more locations relative to patient P1, such as to position recording electrodes 311 relative to a patient. Recording electrodes 311 can be positioned on and/or within garment 50.

In some embodiments, system 10 is configured to generate, receive, and/or process information using two or more modalities (e.g. drive signal and/or received signal modalities), for example: electric potential and ultrasound, electric potential and impedance (e.g. complex impedance such as dielectric properties), and/or other combinations of modalities (e.g. combinations of drive signal and/or received signal forms). One or more transfer matrices of the present inventive concepts can then be generated, and subsequently used (e.g. two or more transfer matrices used in conjunction) to differentiate local, regional, and/or global differences (e.g. temporal and/or spatial differences) that are measured (e.g. insensitively versus sensitively measured) via subsets of each modality employed. For example, spatial or temporal changes in respiratory pattern and/or respiratory volume may be sensitive to both impedance and ultrasound modalities, and yet to a lesser degree to cardiac electric potential modalities, while spatial and/or temporal changes in tissue conductivity would be sensitively measured via impedance while measurements using ultrasound are less sensitive.

System 10 can comprise one or more sensors (e.g. electrodes configured to record electrical activity as defined herein) which are positioned on and/or under the skin of the patient. System 10 can further comprise one or more energy delivery elements (e.g. electrodes configured to deliver an electrical signal as defined herein) which are positioned on and/or under the skin of the patient. In some embodiments, system 10 comprises a vest or other garment, garment 50, which positions one or more sensors, transducers, and/or other functional elements relative to the patient's anatomy. For example, the functional elements positioned in garment 50 can be used to perform one or more diagnostic and/or one or more therapeutic procedures on a patient. In some embodiments, garment 50 comprises one or more sensors configured to record patient physiologic data used to produce diagnostic information selected from the group consisting of: ECG and other cardiac electrical information; blood pressure measurements; blood flow measurements; respiration measurements; heart sound measurements; $pO_2$ measurements; $pCO_2$ measurements; ejection fraction measurements; organ function measurements; brain activity measurements; seizure activity measurements; and combinations of these. In some embodiments, system 10 further includes one or more sensors positioned under the patient's skin (e.g. proximate the heart, brain, and/or other organ), in which data from the skin-contacting sensors and internal sensors are processed (e.g. by algorithm 255) to produce diagnostic output. In some embodiments, system 10 creates a coordinate system to identify anatomical locations of the patient, such as when an Einthoven's triangle is used as a coordinate system. In some embodiments, system 10 creates a coordinate system based on the position of one or more surface electrodes (e.g. based on the position of garment 50 comprising one or more surface electrodes).

In some embodiments, a coordinate system is based on the position of one or more internal electrodes (e.g. a coordinate system based one or more drive electrodes positioned within the heart). In these embodiments, the coordinate system can be configured relative to a drive electrode used as a coordinate reference or origin. Alternatively or additionally, the coordinate system can be configured relative to one or more surface electrodes used as a coordinate reference (e.g. origin). Alternatively or additionally, the coordinate system can be configured relative to an anatomical location (e.g. a structure or boundary) used as a coordinate reference (e.g. origin).

In some embodiments, system 10 comprises one or more sensors on the skin of the patient (e.g. electrodes $311_S$, $321_S$, $411_S$, and/or an electrode-based functional element $99_S$) as well as one or more sensors positioned in the heart of the patient (e.g. electrodes $311_I$, $321_I$, $411_I$, and/or an electrode-based functional element $99_I$. In these embodiments, the sensors (e.g. electrodes) positioned in the heart of the patient, can comprise at least one sensor on the endocardial surface of a heart chamber (e.g. a contacting electrode on the endocardial surface of the left atrium), and at least one sensor positioned in the heart chamber offset from the endocardial wall (e.g. a non-contacting electrode in the left atrium or other heart chamber in the flowing blood offset from all endocardial surfaces). Patient information 95 can be determined based on signals (data) received from one or more of at least one skin surface sensor, at least one endocardial surface contacting sensor, and/or at least one non-contacting sensor.

The electrodes and/or other sensors of system 10 can comprise various shapes, surface areas, and materials of construction. In some embodiments, one or more skin contacting electrodes used to record electrical activity and/or deliver electrical energy (e.g. electrodes $311_S$, $321_S$, $411_S$, and/or an electrode-based functional element $99_S$) comprise one or more materials selected from the group consisting of: platinum-iridium; gold; carbon; a polymer (e.g. a polymer coating); and combinations thereof. In some embodiments, one or more electrodes positioned under the skin of the patient to record electrical activity and/or deliver electrical energy (e.g. electrodes $311_I$, $321_I$, $411_I$, and/or an electrode-based functional element $99_I$) comprise one or more materials selected from the group consisting of: platinum-iridium; gold; carbon; a polymer (e.g. a polymer coating); copper; silver-silver chloride; a conductive gel; and combinations of these.

In some embodiments, the electrodes and/or other sensors of system 10 are positioned on the skin of the patient (e.g. electrodes $311_S$, $321_S$, $411_S$, and/or an electrode-based functional element $99_S$) in a vertical arrangement, a horizontal arrangement, a diagonal arrangement, and/or a spiral arrangement relative to the patient. For example, these sensors can be positioned in these and/or other geometric arrangements via garment 50 (e.g. via secure attachment to garment 50 and/or via pockets of garment 50 that accept the sensors) and are in such an arrangement.

Console 200 can comprise one or more discrete components, such as when console 200 comprises one or more housings which collectively surround the components of processing unit 250, user interface 260, recording assembly 300, and/or signal generator 400. Console 200 can comprise multiple discrete components (e.g. each include a discrete housing) that transfer information, signals, and/or power between those components via wired and/or wireless connections. Console 200 can comprise an assembly configured to be transported from one room to another room (e.g. transported between storage and clinical procedure rooms of a hospital).

Processing unit 250 can comprise one or more components which receive, store, analyze, and/or otherwise process information, such as information recorded by recording assembly 300. Processing unit 250 can comprise one or more components which generate and/or otherwise provide information, such as information provided to signal generator 400, and used by signal generator 400 to produce drive signals (e.g. drive signals 413 for drive electrodes 411). Processing unit 250 can comprise one or more central processing units, such as CPU 251 shown. Processing unit 250 can comprise one or more electronic memory modules, such as memory 252 shown.

CPU 251 can include one or more digital signal processors (DSPs) that can analyze signals received from one or more electrodes or other sensors of system 10, as described here, for calculating patient information (e.g. patient electrical information, patient motion, and the like).

Console 200 can comprise a user interface, user interface 260 shown, which can receive information and/or provide information to a user of system 10, such as a clinician of patient P1 and/or P2 described herein. User interface 260 can comprise one or more user input components, such as an input component selected from the group consisting of: a keyboard; a mouse; a touch screen; a joystick; a haptic controller; a microphone; a switch; a keypad; and combinations of these. User interface 260 can comprise one or more user output components, such as an output component selected from the group consisting of: a display (e.g. a video monitor); a speaker; a tactile transducer; and combinations of these.

Transfer matrix 290 can comprise a characterization of electrical properties of tissue (e.g. bone, fat, skin, lung, blood, and/or connective tissue) between a first set of recording locations (e.g. a first set of recording locations 312) and a set of target locations (e.g. a set of target locations 90).

Transfer matrix 290 of system 10 can be used to calculate patient information at one or more patient locations 90 (e.g. one or more patient skin locations $90_s$ and/or one or more locations internal to the patient, internal locations $90_i$), based on information recorded at one or more recording locations 312 (e.g. one or more patient skin locations $312_s$ and/or one or more locations internal to the patient, internal locations $312_i$).

Transfer matrix 290 represents a matrix in which a series of measurements at a first location (e.g. a set of first locations) can be related to characteristics at a second location (e.g. a set of second locations), the characteristics determined by applying the transfer matrix to the series of measurements at the first location. Transfer matrix 290 can be generated by delivering drive signals (e.g. from areas proximate the second location or otherwise), and by performing recordings at the first location. A number of recordings, at one or more similar or dissimilar anatomical locations, can be performed to create transfer matrix 290.

Transfer matrix 290 represents the mathematical correspondence between measurements made in two separate domains. For example, the two separate domains can comprise: a first domain internal to the patient's body and a second domain external to the patient's body; a first domain on a specific region of the patient's body and a second domain on another region of the patient's body; a first domain internal to an organ within the body of the patient and a second domain external to an organ within the body of the patient; and/or combinations of these. Transfer matrix 290 mathematically describes the relationship between measurements made in a first domain, and characteristics (e.g. tissue characteristics and/or electrical conditions) in the corresponding, second domain. Such a transfer matrix 290, can also describe the relationship between measurements made in the second domain, and characteristics of the first domain. Application of transfer matrix 290 can be used to computationally account for characteristic differences (both static and dynamic, as imposed by physiology and environment as described above) between two domains, and it enables the use of measurements from both domains to be used in conjunction.

In some embodiments, a known electrical signal (electrical potential or current) is emitted from a first drive electrode (e.g. an internal electrode) and recorded by one or more (e.g. all) recording electrodes (e.g. surface electrodes). Subsequently, a known signal is emitted from a second drive electrode (e.g. an internal electrode) and recorded by one or more (e.g. all) recording electrodes (e.g. surface electrodes). In some embodiments, subsequently, a known signal is emitted from a third, fourth, etc. drive electrode, such as until all drive electrodes have been used. This implementation provides a set of drive signals (voltage or current) from all drive electrodes (e.g. all internal electrodes) for each recording electrode (e.g. each surface electrode). In these embodiments, the intrinsic cardiac signals (e.g. atrial electrograms) can be recorded with the same recording electrodes (e.g. body surface electrodes).

The relationship (e.g. ratio) of the drive signal to the recorded second signal serves as a basis for transfer matrix 290, and can be used to determine calculated patient information 95, as described herein. Transfer matrix 290 can be continuously updated (e.g. between measurements made to produce calculated patient information 95), such as to account for changes in: body fluid status; electrolyte concentrations; skin resistance; and/or electrode position (e.g. recording electrode position).

Figure 3:
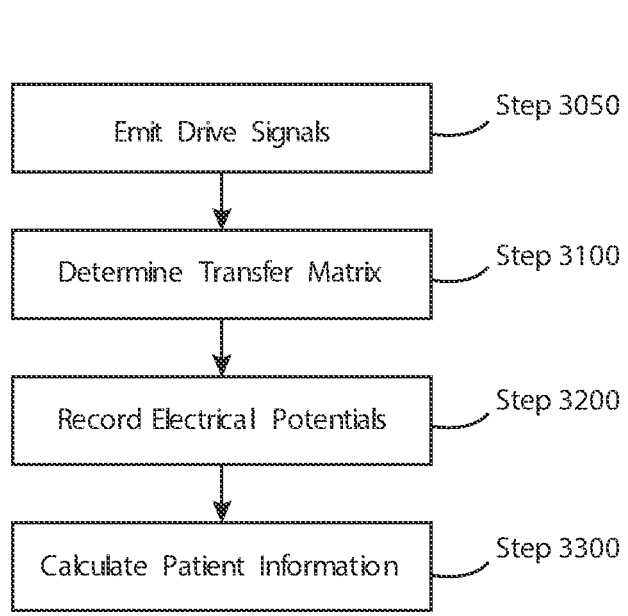
FIG. 3 illustrates a flow chart of a method for determining a transfer matrix and using the transfer matrix to calculate patient information based on recorded signals, consistent with the present inventive concepts.

In some embodiments, system 10 is configured to create transfer matrix 290, such as is described in reference to FIG. 3 herebelow. For example, system 10 can include one or more electrodes or other transducers configured to deliver electrical energy (e.g. deliver a drive signal), such as drive electrodes 411 shown. Drive electrodes 411 can be positioned at various drive locations 412, from which the drive signals 413 are emitted. System 10 can include a set of recording electrodes 321, which can be positioned at multiple recording locations 322, and create a set of recorded signals 323. In FIG. 1, recording locations 322 are the same as recording locations 312 described hereabove (e.g. such as when recording electrodes 311 and 321 are the same set of electrodes or at least one is a subset of the other, such as when patients P1 and P2 are the same patient, such as when electrodes 311 are used to both determine transfer matrix 290 and to determine calculated patient information 95). In other embodiments, recording locations 322 and recording locations 312 comprise different locations (e.g. all the locations are different or at least one is different), such as when locations 322 comprise locations on a different mammalian subject (e.g. used to create a generic transfer matrix 290), or locations 322 comprise different locations on the same patient.

Transfer matrix 290 can be determined (e.g. by algorithm 255) by comparing the set of recorded signals 323 to the set of drive signals 413 emitted from drive locations 412. In some embodiments, drive locations 412 comprise locations within the patient and recording locations 322 comprise locations on the surface (skin) of the patient. Alternatively or additionally, drive locations 412 can comprise locations on the surface of the patient and/or recording locations 322 comprise locations within the patient. In some embodiments, at least one of drive locations 412 and/or recording locations 322 comprise locations both on the surface and within the patient. In some embodiments, at least one of drive locations 412 and/or recording locations 322 is limited to locations on the surface of the patient (i.e. limited to only include locations on the surface of the patient). In some embodiments, at least one of drive locations 412 and/or recording locations 322 is limited to locations within the patient (i.e. limited to only include locations within the patient).

When drive signals 413 are used to determine transfer matrix 290, drive electrodes 411 can comprise at least 1 electrode(s), at least 2 electrodes, and/or at least 48 electrodes, and recording electrodes 321 can comprise at least 4 electrodes, at least 10 electrodes, and/or at least 200 electrodes. In some embodiments, drive electrodes 411 can be positioned at drive locations 412 that are at least 1 mm apart from each other, such as at least 2 mm apart, and/or at least 4 mm apart, and/or at least 10 mm apart, and recording electrodes 321 can be positioned at recording locations 322 that are at least 2 mm apart from each other, such as at least 3 mm apart, at least 10 mm apart, and/or at least 20 mm apart.

In some embodiments, drive locations 412 comprise one or more locations within the patient, such as a drive location selected from the group consisting of: within a chamber of the heart; on endocardial surface of a heart chamber; on epicardial surface of the heart; in a blood vessel (e.g. a vein or artery) of the heart; in the pericardial cavity; in the esophagus; in and/or proximate the brain; in a blood vessel (e.g. a vein or artery) of the brain; and combinations thereof. In these embodiments, device 100 can include one or more drive electrodes 411 (e.g. on a distal expandable basket or other distal portion of device 100), such as when the distal portion of device 100 is inserted into the patient's heart causing drive electrodes 411 to be positioned on the endocardial surface of and/or within a heart chamber. In these embodiments, the associated set of recording locations 322 can comprise locations within the patient, on the skin of the patient, or both. Recording electrodes 321 can be positioned at one or more recording locations 322 selected from the group consisting of: chest; back; torso; shoulder; abdomen; thorax; head; and combinations of these. In some embodiments, system 10 comprises at least 6 recording electrodes.

In some embodiments, recording electrodes 321 comprise surface electrodes 321$_S$ that are positioned to cover the region surrounding the heart in all three dimensions (e.g. anterior-posterior, cranio-caudal and right to left). In some embodiments, the surface electrodes 321$_S$ are configured to deliver signals or other energy to perform localization, cardioversion, and the like (e.g. to avoid a location conflict with a separate electrode used to perform those additional functions).

Alternatively or additionally, drive signals 413 used to determine transfer matrix 290 can be delivered from one or more drive locations 412 that are on the skin of the patient, such as one or more drive locations selected from the group consisting of: chest; back; torso; shoulder; abdomen; thorax; head; and combinations of these. In these embodiments, the associated set of recording locations 322 can comprise locations within the patient, on the skin of the patient, or both. Recording electrodes 321 can be positioned at one or more recording locations 322 selected from the group consisting of: within a chamber of the heart; on endocardial surface of a heart chamber; on epicardial surface of the heart; in a blood vessel (e.g. a vein or artery) of the heart; in the pericardial cavity; in the esophagus; in and/or proximate the brain; in a blood vessel (e.g. a vein or artery) of the brain; and combinations of these.

In some embodiments, at least 4 surface electrodes are used to cover a 3-dimensional volume (e.g. adequately provide drive signals to and/or record signals from a 3-dimensional volume). For example, a set of surface electrodes can comprise: 4 surface electrodes positioned to form a tetrahedron transecting the body; 5 surface electrodes in which 4 form a tetrahedron and the fifth serves as a differentiating electrode out-of-plane with any of the tetrahedral faces; 6 surface electrodes forming 3 orthogonal or near-orthogonal Cartesian axes; 6 surface electrodes wherein 3 surface electrodes form a triangle on one side of the body, and the other 3 surface electrodes form an inverted triangle on an opposing side of the body (e.g. chest and back).

In some embodiments, transfer matrix 290 is determined by one or more drive electrodes 411a delivering a drive signal 413a comprising a first frequency, and one or more drive electrodes 411b delivering a drive signal 413b comprising a different, second frequency. In these embodiments, drive signals 413a and 413b can be delivered simultaneously (e.g. and correspondingly received simultaneously by recording electrodes 321).

In some embodiments, transfer matrix 290 is determined by one or more drive electrodes 411a delivering a drive signal 413a comprising a first frequency, and one or more drive electrodes 411b delivering a drive signal 413b comprising a similar or different, second frequency. In these embodiments, drive signals 413a and 413b can be delivered sequentially (e.g. and correspondingly received sequentially by recording electrodes 321).

In some embodiments, transfer matrix 290 is determined by assessing the magnitude and/or phase of a set of recorded signals 323 (e.g. recorded by recording electrodes 321 positioned at recording locations 322). For example, the transfer matrix 290 can comprise a numerical scale factor which is based on a comparison of the magnitude and/or phase of the set of recorded signals 323 to the magnitude and/or phase, respectively, of a set of drive signals 413 (e.g. delivered by drive electrodes 411 positioned at drive locations 412). In some embodiments, the comparison is based on both magnitude and phase for each set of signals.

In some embodiments, the emitting of drive signals 413 and the associated recording of recorded signals 323 occur over at least one physiologic cycle of the patient, and the resultant transfer matrix 290 comprises a time-dependent (e.g. cycle-time-dependent) transfer matrix. The associated physiologic cycle can comprise a cardiac cycle (e.g. a cycle including systole and diastole), a respiratory cycle, a pressure-varying cycle (e.g. cyclically varying blood pressure), and/or other repeating physiologic cycle of a patient. Recordings can be made over multiple cycles, such as at least 2 cycles, at least 3 cycles, or at least 5 cycles. Transfer matrix 290 can comprise one or more parameters that are proportionally adaptable over time. Transfer matrix 290 can include information as it relates to changes within a physiologic cycle, such as when transfer matrix 290 comprises a time-dependent transfer matrix including one or more components that vary in relative unison with signals recorded by electrodes 311, such as to correlate these recordings made by electrodes 311 over similar physiologic cycles (e.g. a compensation performed when calculating patient information 95 and compensating for variations within a physiologic cycle). In some embodiments, algorithm 255 can be configured to compensate for: a cardiac cycle (e.g. to compensate for heart motion), a respiratory cycle (e.g. to compensate for lung motion and/or other patient respiration parameter), or both. In some embodiments, algorithm 255 calculates patient information 90 by aligning a time-dependent transfer matrix 290 with a physiologic cycle of the patient. Parameters of transfer matrix 290 can vary according to a functional and/or biological process, such as a process which varies cyclically and/or spatially (e.g. blood flow or other cyclically varying cardiovascular process). In some embodiments, one or more parameters of transfer matrix 290 can vary temporally, linearly, and/or exponentially. These parameters can comprise values that are expanding and/or drifting. Variation with time and/or across space does not need to be purely cyclical. These non-cyclic variations can also be modeled, such as a model created via a learning algorithm and trained to compensate for variations. Variations can also be compensated for by extrapolating from previous variation data (e.g. data recorded in patient P1 or a different mammal such as patient P2), such as data configured and used as a comparative model.

In some embodiments, signals recorded during the respiratory cycle (e.g. at a frequency of 10-15 breaths/minute) are averaged and/or signals recorded during the cardiac cycle (e.g. changes due to blood movement and/or systolic movement of heart and heart wall and electrode) are averaged (e.g. at a frequency corresponding to the heart rate) to create transfer matrix 290 (e.g. the averaging resulting in a more stable transfer matrix 290, such as a transfer matrix 290 with improved stability over one or more respiratory and/or cardiac cycles).

In some embodiments, system 10 accounts for one or more physiologic and/or anatomic parameters of the patient (e.g. patient P1 and/or patient P2), such as a parameter selected from the group consisting of: rotation of the heart (e.g. toward the right side or left side of the patient); circumference of the thorax in relation to the heart; location of the heart in the thorax (e.g. low-weight patients have a relatively high positioned diaphragm, emphysema, and COPD patients have a relatively low positioned diaphragm); and combinations of these. These parameters can be determined by analyzing geometric properties of the patient, such as the thoracic circumference (which, as an example, may be calculated based on the distances between surface electrodes, wherein the distances may be determined using impedance-based measurements); the number and angle between the surface electrodes, which surround the body; and/or the rotation and/or location of the heart in relation to the surface electrodes. For example, the standardized position of the surface electrodes (e.g. electrodes used to provide ECG recordings) can be used as a reference, and diagnostic bioelectrical signals measured from surface electrodes may be used in the assessment of physiologic and/or anatomic conditions of the patient. As an example, on a standard 12-lead ECG, the presence of certain signal characteristics in leads V1 or V2 may be indicative of a rightward bias in heart position. Alternatively, signal characteristics in V4-5 may be indicative of a leftward bias of the heart position, and still other signal characteristics may be representative of a higher or lower heart position.

In some embodiments, system 10 modifies transfer matrix 290 at least one time, such as at least one time during a single procedure on a single patient. For example, system 10 can modify transfer matrix 290 intermittently and/or relatively continuously ("continuously" herein) over time, such as in a closed loop fashion. The modification performed by system 10 can be based on at least one patient parameter that varies over time. In some embodiments, the modification performed by system 10 can be based on at least two, or at least three patient parameters that vary over time. The modification performed by system 10 can be based on one or more patient parameters that vary cyclically over time, such as parameters that vary related to the patient's respiratory cycle and/or cardiac cycle. Patient parameters can vary linearly and/or exponentially. In these embodiments, system 10 can include one or more sensors, such as electrodes 311, 321, and/or 411, and/or functional element 99 described herebelow, configured to produce a signal related to the varying patient parameter used to adjust transfer matrix 290. The monitoring can be performed continuously (e.g. such as when transfer matrix 290 is continuously modified), and/or intermittently (e.g. such as when transfer matrix 290 is intermittently modified).

In some embodiments, transfer matrix 290 used on a patient P1 (e.g. to determine patient information 95 based on recorded signals 313) comprises or at least includes information incorporated from a previously calculated (e.g. from at least one other mammalian subject such as patient P2) and/or otherwise standardized transfer matrix, standardized transfer matrix 290'. As used herein, transfer matrix 290 can comprise a standardized transfer matrix 290' (e.g. a transfer matrix based on one or more separate mammals, patient P2). Transfer matrix 290 can comprise a transfer matrix based solely on data from patient(s) P2, based solely on data from patient P1, or a transfer matrix based on data from patient(s) P2 and data from patient P1. In some embodiments, a standardized transfer matrix 290' (or a portion of it) can be selected based on characteristics of the patient for which it is to be used (characteristics of patient P1). For example, multiple different standardized transfer matrices 290' can be determined, each based on one or more mammalian subjects (e.g. patient P2) with one or more particular patient characteristics (e.g. one or more similar patient parameter levels). In some embodiments, a single standardized transfer matrix 290' can accommodate various patient characteristics, such as when this standardized transfer matrix 290' is customized based on one or more particular patient characteristics. A standardized transfer matrix 290' can be chosen and/or customized for use as transfer matrix 290 based on patient P1's parameter levels being similar to the subjects used to create the standardized transfer matrix 290'. In some embodiments, applicable patient parameters used for selection and/or customization comprise parameters selected from the group consisting of: gender; weight; height; body or body portion size; body mass index (BMI); thoracic cavity circumference (e.g. as determined by a functional element 99 comprising an imaging device such as a CT scanner or MRI); location of the esophagus; size of an atrium; filling of an atrial volume; atrial pressure; fat to water ratio; air to water to fat ratio; bone location (e.g. as determined by MRI); medications being taken; level of medication; electrolyte level; pH; $pO_2$; $pCO_2$; water weight; and combinations thereof.

In some embodiments, transfer matrix 290 includes a standardized transfer matrix 290' (e.g. a transfer matrix based on one or more mammals, patient P2, different than patient P1), where differences in locations of recording electrodes on patient P2 used to create the standardized transfer matrix 290' and locations of recording electrodes on patient P1 used to produce calculated patient information 95 are accounted for by system 10.

In some embodiments, a standardized transfer matrix 290' can be derived by analysis of a collection of data sets from multiple (i.e. two or more) patients P2. In some embodiments, the data sets include measured information from each individual patient P2, such as location information (e.g. locations of anatomical structures and/or sensors and other objects), tissue information (e.g. tissue properties, characteristics, and/or qualitative classes), information related to physiologic processes (e.g. respiration and/or cardiac motion and which may include recordings from sensors, and/or data calculated from these recordings, over a period of time), environmental information (e.g. background electrical noise or equipment interconnections) and/or cardiac information (e.g. electrical activation times, conduction patterns, surface charge, dipole density, cardiac potential electrograms (measured as voltage) and the like). In some embodiments, the data sets include transfer matrices 290 calculated from measurements within each individual patient P2 and image data (e.g. CT and/or MRI data) from each individual patient P2. Memory 252 can be used to store the collection of data sets from multiple patients P2. The collection of data sets from multiple patients can encompass a diverse population of patients P2 with varied characteristics (e.g. sex, size, presence of a disease such as emphysema, age, heart location) which can also be included in the patient data sets.

Analysis of the collection of data sets from multiple patients P2 can be performed to identify patterns, correlations, correspondences, and/or other like relationships between the data set elements (such as the measured information, measured transfer matrices 290, the varied patient characteristics, and/or the image data across the collection). This analysis of the collection of data sets can be a 'training' or 'learning' step in a computational and/or algorithmic process, such as a machine-learning method. The analysis yields one or more quantitative entities (e.g. a set of equations or a computational 'model') that describes the complex relationships between the data set elements across the population of patients P2. In some embodiments, the analysis can be performed using computational methods such as: classification, collaborative filtering, regression, clustering, and/or dimensionality reduction and the like. The quantitative entities can be applied in a second step wherein one or more of the data set elements from patient P1 are provided as an input and are then used to compute, select, customize, optimize, update, and/or predict the standardized transfer matrix 290' to use for patient P1. In some embodiments, the data set elements from patient P1 are only a subset of the data set elements used to compute the quantitative entities, thereby reducing or eliminating an acquisition or measurement step for patient P1.

In some embodiments, the standardized transfer matrix 290' computed, selected, customized, optimized, updated and/or predicted for patient P1 has improved accuracy or reduced artifacts as compared to a transfer matrix directly measured in P1, independently, due to potential vulnerabilities or limitations of measurement (such as environmental interference or human error). In some embodiments, the data set elements from patient P1 can be provided a single time to produce a single standardized transfer matrix 290', and/or it can be provided multiple times in succession (e.g. at intervals or continuously), such as to produce multiple standardized transfer matrices 290' that are applied in succession in order to provide dynamic updates of time-variant relationships. In some embodiments, the data set elements used to produce the quantitative entities may contain time-variant information, and the data set elements from patient P1 need only be applied once or a limited number of times in order for multiple standardized transfer matrices 290' to be produced to provide dynamic updates more frequently than information from P1 is provided—thereby providing greater temporal resolution in updating the standardized transfer matrices 290'. In these embodiments, system 10 can produce calculated patient information 95 using a standardized transfer matrix 290' (e.g. transfer matrix 290 comprises a standardized transfer matrix 290' only). In some embodiments, a patient image (e.g. an MRI or CT scan) is not used (e.g. not necessary), such as if a suitable standardized transfer matrix 290' can be chosen and/or customized based on characteristics of patient P1 (e.g. characteristics such as size, weight, thoracic circumference, and/or rotation and/or location of the heart).

In some embodiments, system 10 utilizes dynamic feedback and/or machine learning to determine transfer matrix 290 and/or in using transfer matrix 290 to determine calculated patient information 95 based on recorded signals 313. In some embodiments, the collection of data sets from one or more patients P2 (e.g. to create a standardized transfer matrix 290') can include therapy information. For example, standardized transfer matrix 290' can be based on one, two, or more therapy parameters selected from the group consisting of: duration (e.g. duration of energy delivery); intensity (e.g. intensity of energy delivery); amplitude (e.g. amplitude of energy delivery); temperature (e.g. temperature of tissue receiving energy); power (e.g. power of energy delivery); impedance (e.g. impedance of tissue); and combinations of these. Each parameter can be analyzed in absolute, relative, and/or differential forms. Standardized transfer matrix 290' can be based on a tissue parameter (e.g. tissue parameter information 80 stored by system 10) related to the applied therapy, such as one, two, or more tissue parameters (e.g. parameters of tissue receiving ablation energy and/or other treatment) selected from the group consisting of: size; depth; thickness; density; composition; and combinations of these. Standardized transfer matrix 290' can be based on the effectiveness of a therapy (e.g. an ablation therapy) on local and/or regional electrical properties of tissue. Standardized transfer matrix 290' can be based on acute (i.e. short-term) effectiveness and/or chronic (e.g. long-team) effectiveness of a therapy. Applicable short-term and/or long-term therapy effectiveness parameters include but are not limited to: elimination of conduction; change in conduction, velocity, amplitude, and/or direction of electrical signals in tissue; change in measured electrical signal amplitude, frequency, and/or rate; change in rate, pattern, and/or frequency of a cardiac cycle; conversion of a cardiac rhythm; change in duty cycle and/or duration of an intermittent rhythm; maintenance of a desired cardiac rhythm; conversion to an alternate rhythm (e.g. a desired or undesired rhythm); and/or duty factor of a resultant rhythm (e.g. a desired or undesired rhythm). Standardized transfer matrix 290' can be based on a short-term and/or long-term therapy effectiveness parameter related to a change in local, regional, and/or global mechanical and/or functional properties of tissue, such as a parameter related to: a change or maintenance of cardiac output and function; and/or a change in tissue stiffness, contractility, displacement, and/or strain. The analysis of the collection of data sets from one or more patients P2, as described hereabove, can be performed by system 10 (e.g. by algorithm 255) and the results used to provide calculated patient information 95 to compute, select, customize, predict, update, and/or otherwise enhance therapy (e.g. therapeutic energy delivery and/or pharmaceutical therapy strategy) for patient P1. In some embodiments, transfer matrix 290 is based on a reduced set of data (a subset of a complete data set) recorded from patient P1, which is used in combination with data (e.g. a full set) recorded from one or more patients P2. In these embodiments, enhancement of therapy can be achieved without acquisition or other measurement of the remaining data set from patient P1, thereby reducing cost, time, and/or procedural complexity. For example, assessments of one or more lesions created during a treatment procedure can be eliminated or at least reduced, based on the included patient P2 data.

In some embodiments, system 10 utilizes machine learning, such as is described hereabove. System 10 can be configured to obtain sequential measurements from one or more (e.g. all) surface electrodes configured to record sequentially emitted signals from each of one or more internal electrodes, and to track changes (e.g. physiologic changes correlating to signal changes) over time. System 10 can assess respiratory and/or cardiac cycles, and it can perform compensation (e.g. subtraction and/or cancellation) to reduce undesired effects of these variations (e.g. as described hereabove). System 10 can determine heart movement throughout the cardiac cycle by assessing changes of impedance between internal electrodes and surface electrodes. This heart movement determination can be used to calculate mechanical, dynamic, and/or other functional characteristics of the heart, such as contractility, volume, volume changes over time, ejection fraction, wall motion, wall displacement, strain, and/or pressure, and it can be used to monitor heart function during the clinical procedure (e.g. to assess safety of the procedure). In some embodiments, the function of the ventricle can be measured, such as by measuring transthoracic impedance (e.g. combined with signals provided and/or recorded by internal electrodes). The atrial and the ventricular function can be separated by a time window: such as when ventricular function is assessed 200 ms to 500 ms after the QRS complex, when systole takes place. In some embodiments, the geometry of the thorax (e.g. diameter, circumference, volume, and the like) is determined based on measurements made by two or more surface electrodes, and changes to the geometry in relation to respiration (e.g. changes related to respiratory excursion and/or respiratory frequency). In some embodiments, measurement of location of heart in relation to surface electrodes (e.g. a 12 lead ECG, electrodes 311, 321, and/or 411 positioned on the skin), as well as the heart's rotation, position and/or displacement (e.g. up and down) during respiration and cardiac contraction. Heart movement during systole can be determined in different heart rhythms (e.g. sinus rhythm, flutter, and/or fibrillation). System 10 can integrate anatomical information (e.g. from CT, MRI, ultrasound, and/or other imaging device) into transfer matrix 290 (e.g. information related to air/fat/water ratio; location of bones, vertebral column, and/or ribs; dimensions of thorax diameter; and/or angle and/or rotation of the heart) along with other information (e.g. ECG information, and/or signal axis of body surface electrodes). System 10 can be configured to create transfer matrix 290, and it can also be configured to update (e.g. adapt or otherwise modify) transfer matrix 290 (e.g. update transfer matrix 290 continuously or at least repeatedly). System 10 can be configured to perform a localization procedure, such as to determine the location of one or more electrodes (e.g. internal drive and/or internal recording electrodes) relative to a localization coordinate system.

In some embodiments, system 10 is configured to deliver a vector pulse of energy from one or more electrodes positioned on the skin of the patient (e.g. one or more of electrodes $311_S$, $321_S$, $411_S$, and/or electrode-based functional elements $99_S$) to one or more electrodes positioned within the patient (e.g. one or more of electrodes $311_I$, $321_I$, $411_I$, and/or electrode-based functional elements $99_I$), such as one or more electrodes integrated onto a distal portion of device 100. In these embodiments, the one or more skin electrodes can immediately begin recording after delivery of the vector pulse (and/or separate skin electrodes can record) such as to determine characteristics of the tissue based on the recordings, such as to determine electrical conduction properties and/or physical properties (e.g. scar, fibrosis, fiber orientation, and the like) based on the response of the tissue to the vector pulse. Electrical activation of tissue can be detected immediately in the region of tissue around an intracardiac catheter. This method is analogous to the CRT-devices that use electrical vectors to activate tissue from a housing (e.g. an implantable metal housing) to a lead. Magnitude and phase information can also be acquired to determine if the impulse activated the region of tissue in the direction of the vector. This determination can be performed for a subset of surface electrodes to an intracardiac electrode to determine if the tissue in the direction of the vector is viable. This vector is rotated around the patient's body and/or modulated by creating a vector using different subgroups of the surface electrodes to the intracardiac catheter electrode to create a 3D map of the viability of tissue. Alternatively or additionally, system 10 can be configured to deliver a vector pulse of energy between surface electrodes.

Recording assembly 300 can be integral to console 200 and/or it can comprise a second standalone console operably attached to console 200.

Recording assembly 300 can be configured to record signals of one or more electrodes or other sensors of system 10, such as recording electrodes 311. Recording assembly 300 can record signals from one or more other electrodes of system 10, such as an electrode that is also configured as a drive electrode, such as drive electrode $411_S$ comprising one or more drive electrodes on the skin of the patient, and/or drive electrode $411_I$ comprising one or more electrodes positioned within the patient (e.g. when included on patient-inserted device 100). Recording assembly 300 can be connected to one or more electrodes via wired or wireless connections as shown in FIG. 1 (connection to recording electrodes 311 and 321 shown via solid lines, and connection to drive electrodes 411 shown via dashed line connected to solid line).

Recording assembly 300 can include circuitry, patient isolation circuitry 301 shown, configured to isolate a patient (e.g. patient P1 or P2 shown) from undesired electrical shock or other undesired interaction with recording assembly 300. Recording assembly 300 can include one or more analog-to-digital converters, A2D 302 shown, which can be configured to convert recorded analog signals to digital signals (e.g. digital signals received by processing unit 250 from recording assembly 300). Recording assembly 300 can include one or more signal filters, filter 303 shown, which can be configured to filter out undesired noise or other undesired signals. Recording assembly 300 can include other signal recording and/or other signal processing circuitry known to one of skill in the art, such as a wireless receiver configured to receive wireless signals from garment 50, a wirelessly transmitting electrode of system 10, and/or another wireless transmitter.

In some embodiments, recording assembly 300 is configured to multiplex (e.g. includes multiplexing circuitry) connections to multiple sensors, such that a first set of one or more sensors (e.g. electrodes configured to record electrical activity) are recorded for a first time period, after which a second set of one or more sensors (e.g. electrodes configured to record electrical activity) are recorded for a subsequent second time period. In some embodiments, three or more sets of sensors are multiplexed.

Recording assembly 300 can be configured to perform dynamic impedance and/or dynamic voltage measurements related to the patient's respiratory cycle and/or physiologic cycle changes, as described hereabove.

Recording assembly 300 can be configured to record from multiple electrodes collectively (e.g. via multiplexing or other scheme) to form "macroelectrodes", such as to take advantage of electrical and/or geometric advantages of more than one electrode and/or more than one recording channel. Examples of some advantages include larger effective electrode surface area (from multiple electrodes) and lower input impedance (through multiple parallel recording channels).

Recording electrodes 311 can include one or more electrodes placed on the skin of the patient, electrodes $311_s$ shown, and/or one or more electrodes placed within the patient, electrodes $311_i$ shown. Recording electrodes 311 can comprise two or more electrodes, such as at least 2, at least 4, at least 6, or at least 10 electrodes.

In some embodiments, recording electrodes 311 comprise at least 3 electrodes (e.g. 3 electrodes included in a standard 6 limb-lead used for ECG recordings). In some embodiments, recording electrodes 311 comprise at least 9 electrodes (e.g. 9 electrodes included in a standard 12-lead ECG). In some embodiments, recording electrodes 311 comprise no more than 1000 electrodes (e.g. up to 1000 surface electrodes included in garment 50, such as at least 50 electrodes, at least 100 electrodes, and/or at least 250 electrodes positioned in garment 50). In some embodiments, recording electrodes 311 are positioned in a relatively uniform pattern on the surface of the patient (e.g. a uniform pattern provided by garment 50). The number of recording electrodes 311 can be determined by the use of the coordinate system used, such as when at least 2 electrodes 311 (e.g. at least 2 surface electrodes) are used for each axis of the coordinate system used.

Recording electrodes 311 can include one, two, or more electrodes positioned on the skin of the patient, such as at locations $312_S$ selected from the group consisting of: chest; back; torso; shoulder; abdomen; skull; face; arm; leg; groin; and combinations of these. In these embodiments, target locations 90 can comprise one or more locations within the patient, such as one or more locations on and/or within an organ of the patient. For example, recording locations 312 can comprise one or more locations selected from the group consisting of: chest; back; torso; shoulder; and/or abdomen; and the target locations 90 can comprise one or more heart locations; such as a heart location selected from the group consisting of: epicardial surface of the heart; within heart tissue (subendocardial); endocardial surface of a heart chamber; within a heart chamber; pericardial cavity; pericardium; and combinations thereof. In some embodiments, recording electrodes 311 comprise at least one electrode positioned in each of the following locations: in the cardiac chamber, on the skin, and in the esophagus. In some embodiments, recording electrodes 311 comprise one internal location and at least one non-intracardiac location (e.g. a location on the skin surface, a location on the epicardial surface, and/or a location on the pericardial surface). In some embodiments, recording electrodes 311 comprise at least 9 or at least 12 recording electrodes 311 (e.g. 9 or 12 electrodes further configured as a 12-lead EKG device).

Recording electrodes 311 can include one, two, or more electrodes positioned on the skin of the patient at locations $312_S$ via garment 50. Garment 50 can be configured to position the recording electrodes 311 at various positions relative to each other, and/or relative to the anatomy of the patient.

Recording electrodes 311 can include one, two, or more electrodes positioned within the patient, such as at recording locations $312_I$ on and/or within an organ of the patient. In some embodiments, recording locations $312_I$ comprise heart locations selected from the group consisting of: locations within a chamber of the heart; locations on an endocardial surface of the heart; locations on an epicardial surface of the heart; and combinations thereof. In some embodiments, recording locations $312_I$ comprise one or more locations selected from the group consisting of: esophagus; epicardium (e.g. accessed via a transthoracic or subxiphoid approach); pericardium (e.g. via a subxiphoid approach); proximate but external to the heart; and combinations thereof. In some embodiments, recording locations $312_I$ comprise locations containing interstitial fluid (e.g. tissues surrounding the heart and/or subcutaneous tissue locations). In some embodiments, recording locations $312_I$ comprise locations within and/or at least proximate the spine and/or locations within and/or at least proximate the brain.

In some embodiments, recording electrodes 311 comprise at least one recording electrode positioned on the skin of the patient, and at least one recording electrode positioned within the patient. In these embodiments, externally-placed recording electrodes $311_S$ (e.g. on the skin) and internally placed recording electrodes $311_I$ (e.g. within the patient) can be multiplexed to provide source (e.g. provide function as a recording electrode) and/or sink (e.g. provide function as a drive electrode). Multiplexing of electrodes (e.g. recording electrodes 311) can be performed to form a group of electrodes that function as a single source and/or a single sink.

In some embodiments, recording electrodes 311 comprises one, two, three, or more electrodes selected from the group consisting of: body surface electrodes; intrabody electrodes (e.g. electrodes placed within the body, under the patient's skin); percutaneous electrodes; subcutaneous electrodes; epicardial electrodes; pericardial electrodes; spine electrodes; brain electrodes; and combinations of these.

In some embodiments, recording electrodes 311 comprises one, two, three, or more electrodes selected from the group consisting of: one or more electrodes configured to emit and/or receive a localization signal; multiple electrodes configured to produce an ECG signal, such as at least 9 electrodes of a 12-lead ECG device; multiple electrodes configured to produce a high density ECGi signal; one or more electrodes configured to deliver cardiac pacing energy; one or more electrodes configured to deliver defibrillation energy; one or more electrodes configured to deliver therapeutic energy; and combinations of these (e.g. such as to avoid the need for standard ECG patch electrodes, pacing components, and/or defibrillation components).

In some embodiments, recording electrodes 311 are configured to emit and/or receive a localization signal, such as a localization signal used to identify the position of one or more devices positioned within the patient (e.g. device 100 described herein). For example, signal generator 400 can provide a localization signal to drive electrodes 411 that is received by recording electrodes 311. Additionally or alternatively, signal generator 400 can be electrically attached to recording electrodes 311 (e.g. via a conduit represented by the dashed line), and signal generator 400 can provide a localization signal to recording electrodes 311 (e.g. that is received by drive electrodes 411, electrodes 321, and/or other electrode of system 10).

In some embodiments, recording electrodes 311 are positioned (relative to the patient) in a defined pattern (e.g. a standardized pattern), such as a pattern defined by a coordinate system. For example, one or more recording electrodes 311 can be positioned in garment 50, and garment 50 positioned relative to the patient, to position recording electrodes 311 in a particular pattern relative to the patient (e.g. the coordinate system can be standardized via garment 50).

In some embodiments, recording electrodes 311 comprise one or more electrodes further configured to record an ECG signal of the patient, such as when recording electrodes 311 comprise: at least 9 electrodes of a 12-lead ECG device and/or multiple electrodes configured to produce a high density ECGi signal. Recording electrodes 311 can be configured to provide arrhythmia monitoring of the patient. In these embodiments, the recording electrodes 311 can be specifically positioned relative to the patient's anatomy by garment 50.

In some embodiments, recording electrodes 311 are further configured to deliver pacing energy and/or defibrillation energy to the patient, such as pacing energy and/or defibrillation energy provided by signal generator 400. In these embodiments, the recording electrodes 311 can be specifically positioned relative to the patient's anatomy by garment 50.

Recording electrodes 321 can include one or more electrodes placed on the skin of the patient, electrodes $321_s$ shown, and/or one or more electrodes placed within the patient, electrodes 321$_i$ shown. Recording electrodes 321 can comprise two or more electrodes, such as at least 2, at least 4, or at least 10 electrodes. In some embodiments, recording electrodes 321 comprise at least two times the number of axes present in a coordinate system used by system 10, and/or recording electrodes 321 comprise a quantity of electrodes that is at least one more than the number of axes present in a coordinate system (e.g. 4 electrodes for a 3-axis coordinate system). In some embodiments, recording electrodes 321 comprise at least 9 electrodes (e.g. at least 9 electrodes further configured as a standard 12-lead ECG device). In some embodiments, recording electrodes 321 comprise at least 3 electrodes (e.g. 3 electrodes further configured as a standard 6 limb-lead ECG).

Recording electrodes 321 can include one, two, or more electrodes positioned on the skin of the patient, such as at locations 322$_S$ selected from the group consisting of: chest; back; torso; shoulder; abdomen; skull; face; arm; leg; groin; and combinations of these. In some embodiments, recording electrodes 321 comprise at least one electrode positioned in each of the following locations: limbs of the patient (e.g. on the leg or arm of the patient), and torso of the patient (e.g. at least 2, 4, or 6 electrodes across the torso of the patient).

Recording electrodes 321 can include one, two, or more electrodes positioned on the skin of the patient at locations 322$_S$ via garment 50. Garment 50 can be configured to position the recording electrodes 321 at various positions relative to each other, and/or relative to the anatomy of the patient.

Recording electrodes 321 can include one, two, or more electrodes positioned within the patient, such as at recording locations 322$_I$ on and/or within an organ of the patient. In some embodiments, recording locations 322$_I$ comprise heart locations selected from the group consisting of: locations within a chamber of the heart; locations on an endocardial surface of the heart; locations on an epicardial surface of the heart; and combinations thereof. In some embodiments, recording locations 322$_I$ comprise one or more locations selected from the group consisting of: esophagus; epicardium (e.g. accessed via a transthoracic or subxiphoid approach); pericardium (e.g. via a subxiphoid approach); proximate but external to the heart; and combinations thereof. In some embodiments, recording locations 322$_I$ comprise locations containing interstitial fluid (e.g. tissues surrounding the heart and/or subcutaneous tissue locations). In some embodiments, recording locations 322$_I$ comprise locations within and/or at least proximate the spine, and/or locations within and/or at least proximate the brain.

In some embodiments, recording electrodes 321 comprise at least one recording electrode positioned on the skin of the patient, and at least one recording electrode positioned within the patient. In these embodiments, externally-placed recording electrodes 321$_S$ (e.g. on the skin) and internally placed recording electrodes 321$_I$ (e.g. within the patient) can be multiplexed to provide source (e.g. provide function as a recording electrode) and/or sink (e.g. provide function as a drive electrode). Multiplexing of electrodes (e.g. recording electrodes 321) can be performed to form a group of electrodes that function as a single source and/or a single sink.

In some embodiments, recording electrodes 321 comprises one, two, three, or more electrodes selected from the group consisting of: body surface electrodes; intrabody electrodes; percutaneous electrodes; subcutaneous electrodes; epicardial electrodes; pericardial electrodes; spine electrodes; brain electrodes; and combinations of these.

Signal generator 400 can be electrically attached to recording electrodes 321 (e.g. via a conduit represented by the dashed line), and signal generator 400 can provide a drive signal (e.g. drive signal 413) or other electrical energy to recording electrodes 321 (e.g. that is received by drive electrodes 411, electrodes 311, and/or other electrode of system 10).

In some embodiments, recording electrodes 321 are positioned (relative to the patient) in a defined pattern (e.g. a standardized pattern), such as a pattern defined by a coordinate system. For example, one or more recording electrodes 321 can be positioned in garment 50, and garment 50 positioned relative to the patient, to position recording electrodes 321 in a particular pattern relative to the patient (e.g. the coordinate system can be standardized via garment 50).

Signal generator 400 can be integral to console 200 and/or it can comprise a second standalone console operably attached to console 200.

Signal generator 400 is configured to produce signals provided to one or more electrodes or other transducers of system 10, such as drive electrodes 411.

Signal generator 400 can include circuitry, patient isolation circuitry 401 shown, configured to isolate a patient (e.g. patient P1 or P2 shown) from undesired electrical shock or other undesired interaction with signal generator 400. Signal generator 400 can include one or more digital-to-analog converters, D2A 402 shown, which can be configured to convert digital signals (e.g. digital information received from processing unit 250) to analog signals. Signal generator 400 can include one or more signal filters, filter 403 shown, which can be configured to filter out undesired noise or other undesired signals. Signal generator 400 can include other signal generator and/or other signal processing circuitry known to one of skill in the art.

In some embodiments, signal generator 400 is configured to provide a localization signal, such as a localization signal provided to drive electrodes 411, recording electrodes 311 (e.g. recording electrodes 311 positioned in garment 50), and/or other electrodes of system 10.

In some embodiments, signal generator 400 is configured to provide energy to pace and/or defibrillate the heart of the patient, such as pacing and/or defibrillation energy provided to recording electrodes 311 (e.g. recording electrodes 311 positioned in garment 50), drive electrodes 411, functional element 99, and/or other electrodes of system 10.

In some embodiments, signal generator 400 is configured to multiplex (e.g. includes multiplexing circuitry) connections to multiple transducers, such that a first set of one or more transducers (e.g. electrodes configured to deliver an electrical signal and/or other electrical energy) are provided energy for a first time period, after which a second set of one or more transducers (e.g. electrodes configured to deliver an electrical signal and/or other electrical energy) are provided energy for a subsequent second time period. In some embodiments, three or more sets of transducers are multiplexed. Drive electrodes can be configured (e.g. via multiplexing or another scheme) to be interconnected to form macroelectrodes, as described hereabove. Grouping of drive electrodes can be patterned to provide geometric and/or electrical advantages, for example, shaping the sourced field in the body, maximizing linearity of a sourced field, maximizing field curvature of a sourced field, and/or maximizing or minimizing edge effects by creating or eliminating 'holes' in the electrode group.

In some embodiments, signal generator 400 transmits from a first set of electrodes positioned within the patient (e.g. electrodes $411_I$) while recording assembly 300 simultaneously records signals from a second set of electrodes positioned on the skin of the patient (e.g. electrodes $311_S$), after which signal generator 400 transmits from the second set of electrodes positioned on the skin of the patient (e.g. electrodes $311_S$) while simultaneously recording signals from the first set of electrodes within the patient (e.g. electrodes $411_I$). This alternating sourcing and sinking can be continued for multiple cycles. In some embodiments, algorithm 255 is configured to determine timing of each portion of the cycle, and/or to determine in which electrodes to deliver a signal and record a signal. The combination of multiplexing to achieve source and sink variations of the electrodes of system 10 allows flexibility in establishing, shaping, and/or modulating the geometric orientation and shape of the source and sink signal paths (e.g. a field) through the body. The geometric orientation and shape of the signal paths through the body can be varied as a function of time to produce a spatio-temporally varying sequence or pattern.

In some embodiments, at least one drive electrode 411 is positioned on the skin of the patient (e.g. via garment 50), and potentially maintained in position by garment 50 (e.g. garment 50 comprises one or more drive electrodes 411). In these embodiments, drive electrode 411 can be configured to deliver a drive signal 413 that is used to determine transfer matrix 290 (as described herein), to deliver a localization signal, to deliver cardiac pacing energy, to deliver defibrillation energy, deliver therapeutic energy (e.g. deliver energy to suppress a seizure, headache, or other neurological condition and/or otherwise treat an adverse patient condition), and/or to perform another function.

Device 100 can comprise one or more devices configured for insertion into a patient (e.g. into the vasculature system of the patient and/or otherwise under the skin of the patient). In some embodiments, device 100 includes a distal portion configured for insertion into a chamber of the heart of patient P1. Device 100 can include a set of electrodes configured to provide a drive signal, drive electrodes 411.

Device 100 can comprise a mapping and/or an ablation device, such as an ablation device that is localized via a localization signal provided by system 10 (e.g. a localization signal delivered by recording electrodes 311).

Garment 50 can comprise one or more different forms that position one or more of the recording electrodes 311 at locations relative to the patient's anatomy (e.g. on the skin of the patient at particular anatomical positions). Garment 50 can comprise a garment selected from the group consisting of: vest; shirt; strap; belt; and combinations of these.

Garment 50 can comprise a wireless transmitter (e.g. functional element $99_S$ configured as a wireless transmitter), such as a wireless transmitter configured to wirelessly transmit recordings made by one or more electrodes and/or other sensors of garment 50 to a receiving element of recording assembly 300.

In some embodiments, system 10 utilizes one or more electrodes of garment 50 (e.g. one or more electrodes $311_S$, $321_S$, $411_S$, and/or electrode-based functional elements $99_S$) to perform impedance tomography of the patient's torso.

In some embodiments, garment 50 is configured simply as a template, such as when garment 50 is placed on the patient to mark locations for sensor placement, and/or includes openings through which sensors are placed on the skin of the patient (e.g. after which garment 50 is removed).

Calculated patient information 95 can comprise a map of electrical activity of an organ of a patient, such as the heart or brain. Mapped electrical activity can include voltage information, dipole density information, and/or surface charge information. In cardiac applications, the target locations 90 associated with the calculated patient information 95 can include locations on the endocardial surface, locations within heart tissue, and/or locations on the epicardial surface. In brain applications, the target locations 90 associated with the calculated patient information 95 can include locations on the surface of the brain and/or within the brain (e.g. in the cerebral cortex and/or within the deep brain).

Calculated patient information 95 can comprise information types selected from the group consisting of: electrical information (e.g. voltage information, surface charge information, tissue charge information, and/or dipole density information); tissue; structural or mechanical information (e.g. density, and/or a difference in a mechanical property such as density, size, and/or shape of a region of a change in a mechanical property such as density); tissue composition information (e.g. damaged tissue, inflamed tissue, and/or denatured tissue, such as denatured protein, collagen, fibrosis, fat, and/or nerves); electrographic flow information; impedance information; phase information (e.g. for phase mapping); and combinations of these. For example, calculated patient information 95 can comprise tissue density information which has been modified in a tissue ablation procedure (e.g. an RF or other cardiac tissue ablation procedure to treat an arrhythmia), such as to assess the quality of the ablation performed. In some embodiments, calculated patient information 95 can comprise a combination of electrical information (such as surface charge information) and mechanical and/or compositional properties of tissue (density or presence of denatured protein or other indicators of structural formation of an ablation lesion or other treated tissue), such that the effectiveness of a delivered therapy can be categorized as complete or incomplete. For example, electrical information gathered by system 10 can indicate loss of electrical conduction while structural formation of a lesion (e.g. a lesion created via delivery of ablation energy) remains incomplete, which may indicate a lesion that is only temporarily effective (e.g. undesired conduction may reoccur in the future). Gathered electrical information can indicate continued conduction through a treated area and mechanical and/or compositional information can suggest the formation of edema rather than a fully transmural (ablation) lesion which may motivate a change in therapeutic strategy. Gathered electrical information can indicate elimination of electrical conduction through an area and structural and/or compositional information can indicate formation of a fully transmural (ablation) lesion, which may increase the probability that the lesion will remain effective for long periods of time, which increases confidence in the therapy delivered.

As described hereabove, calculated patient information 95 can comprise tissue composition information. Tissue composition can be locally assessed by system 10 via optical measurement (e.g. spectroscopically or fluoroscopically). System 10 can be configured to determine fluorescence, reflectance, and/or absorption from tissue (e.g. using a fiber-optic or a CCD camera enabled catheter). System 10, via algorithm 255, can assess the degree to which the tissue fluoresces, reflects, and/or absorbs light. These responses to particular two or more wavelengths of light can add further specificity, as different biomaterial compositions fluoresce, reflect, and/or absorb light in specific ways. In some embodiments, system 10 analyzes a lesion by monitoring for the fluoroscopic signature of NADH. NADH is a coenzyme that is present within all intact cells and fluoresces when illuminated with certain wavelengths of light (such as UV).

Once cells are damaged (e.g. by RF ablation), NADH is released from the mitochondria of the cells and/or converted to its oxidized form, and its fluorescence markedly declines. Under some therapeutic methods, cell damage is the desired outcome of a clinical procedure (e.g. an ablation procedure configured to treat an arrhythmia such as atrial fibrillation). However, the tissue and/or other body response to the therapy under some conditions can vary. For example, while attempting to deliver RF ablation to cardiac tissue, the inflammatory response of the body accumulates extracellular fluid to the affected area (edema), thereby protecting the cells from further damage. This edema can prohibit efficient delivery of further RF energy and therefore reduce the effectiveness of subsequent delivery of ablation energy. When edema forms, the cells are left intact, and the fluoroscopic signature of NADH remains unchanged, so this fluoroscopic measurement performed by system 10 is highly specific for the desired response of tissue to delivered ablation energy (e.g. where cell damage correlates to lesion formation). This analysis can be performed in combination with an assessment of tissue density (also at the energy delivery location), to further refine the assessment of cell damage versus healthy tissue. In some embodiments, system 10 creates a standardized transfer matrix 290' based on one or more patients P2, by recording treatment information related to an ablation procedure (e.g. a cardiac ablation procedure) performed on the patients P2. The treatment information can include: electrical information; anatomy information (e.g. as recorded by an imaging device); tissue impedance information. This information can be combined with measurements of tissue composition, and then system 10 (e.g. using a machine learning algorithm) can sensitively and specifically identify hallmarks of tissue composition, which can be correlated to a procedure performed on patient P1, without having to do the actual measurement of composition directly in patient P1.

In some embodiments, calculated patient information 95 comprises dipole density and/or surface charge information that is determined (e.g. by algorithm 255) using the devices and methods such as is described in applicant's co-pending U.S. patent application Ser. No. 16/533,028, titled "Method and Device for Determining and Presenting Surface Charge and Dipole Densities on Cardiac Walls", filed Aug. 6, 2019, and/or applicant's co-pending U.S. patent application Ser. No. 16/568,768, titled "Device and Method for the Geometric Determination of Electrical Dipole Densities on the Cardiac Wall", filed Sep. 12, 2019, the content of each of which is included herein by reference in its entirety for all purposes.

In some embodiments, calculated patient information 95 comprises information types selected from the group consisting of: medication information; electrolyte information; pH information; and combinations thereof.

In some embodiments, system 10 is configured to gather other physiologic data of the patient (e.g. data other than that recorded by recording electrodes 311, 321 and/or drive electrodes 411). In these embodiments, system 10 can include functional element 99 comprising one, two, three, or more sensors or other data acquiring components. In some embodiments, functional element 99 can comprise one or more sensors or other functional elements positioned within the patient, functional element $99_I$, and/or one or more sensors or other functional elements positioned on the patient's skin, functional element $99_S$, each as shown. Functional element $99_S$ can comprise one or more functional elements positioned on and/or within garment 50 (as shown in FIG. 1). Functional element $99_I$ can comprise one or more functional elements positioned on and/or within device 100 (e.g. on a basket or other distal portion of device 100 as shown).

In some embodiments, functional element 99 comprises one or more components configured to gather data selected from the group consisting of: physiologic cycle data; cardiac data; respiration data; patient medication data; skin impedance data; perspiration data; thoracic and/or abdominal cavity dimensional data (e.g. as measured manually and/or by an imaging device such as a CT or MRI); water weight data; hematocrit level data; wall thickness data (e.g. cardiac wall thickness data); and combinations of these. For example, functional element 99 can comprise a manual measurement device (e.g. a tape measure or ruler) and/or an imaging device (e.g. a CT or MRI) that is used to collect thoracic cavity measurement information used by system 10 to determine transfer matrix 290 and/or calculated patient information 95. In some embodiments, functional element 99 comprises one, two, three, or more sensors selected from the group consisting of: magnetic sensor; water sensor; perspiration sensor; skin impedance sensor; glucose sensor; pH sensor; $pO_2$ sensor; $pCO_2$ sensor; $SpO_2$ sensor; heart rate sensor; pressure sensor; blood pressure sensor; spine sensor; brain electrode; brain sensor; flow sensor; blood flow sensor; movement sensor; and combinations of these. In these various embodiments, algorithm 255 can be configured to include this additional patient information, such as in an analysis to calculate patient information 95, to determine and/or modify transfer matrix 290 (e.g. to modify transfer matrix 290 in a continuous and/or intermittent manner), to determine and/or modify a system 10 parameter; and/or to perform another function. In some embodiments, transfer matrix 290 is used to measure cardiac function (e.g. change of blood volume over time) as described herein, such as during a cardiac ablation or other heart procedure.

In some embodiments, functional element 99 comprises one or more electrodes or other transducers configured to deliver an electrical signal and/or electrical energy to the patient. For example, functional element 99 can comprise one or more electrodes configured to: deliver a drive signal (e g similar to drive signal 413) that is used to determine transfer matrix 290 (as described herein); deliver a localization signal; deliver cardiac pacing energy; deliver defibrillation energy; and/or to perform another function.

In some embodiments, functional element 99 comprises one or more magnets used by system 10 for spatial tracking (e.g. respiration tracking and/or other patient movement tracking). In these embodiments, garment 50 can comprise the one or more magnets, such as to position the one or more magnets at one or more pre-determined locations relative to the patient.

In some embodiments, functional element 99 comprises one or more ultrasound elements (e.g. sensors and/or transducers) used to measure distances, such as to create a 2D or 3D image of patient tissue and/or devices of system 10 positioned on and/or within the patient. In these embodiments, garment 50 can comprise the one or more ultrasound elements, such as to position the one or more ultrasound elements at one or more pre-determined locations relative to the patient.

In some embodiments, functional element 99 comprises a microphone for recording heart sounds, such as a microphone integrated into patient garment 50 to position the microphone at a particular location relative to the patient.

In some embodiments, functional element 99 comprises an accelerometer such as an accelerometer configured to track motion of a portion of the patient (e.g. when integral to garment 50), and/or an accelerometer included in another component of system 10 (e.g. included in device 100 to track patient tissue motion and/or device 100 motion).

In some embodiments, one or more drive electrodes of system 10 positioned within the patient (e.g. within the patient's heart) at one or more known locations (e.g. in the blood within the chamber, offset from the heart wall), emit drive signals (e.g. one or more drive signals) of known magnitude. System 10 includes one or more recording electrodes positioned on the skin surface of the patient at one or more locations (e.g. one or more arbitrary locations), which measure a response to the drive signals. The ratio of these recorded signals to the drive signals can be used by system 10 to produce transfer matrix 290. These ratios depend on various patient characteristics (e.g. obesity, size of heart, conduction of lung, organs, and other tissue, skin resistance, orientation of the heart, respiratory changes, diaphragmatic location, and the like). Subsequently, electrical activity (e.g. cardiac electrical activity) is measured simultaneously with both internal electrodes and surface electrodes (e.g. the same used previously or otherwise). Using transfer matrix 290, system 10 transforms the electrical activity measured by the surface electrodes to produce a first map of potentials on the heart wall (e.g. as a ratiometric proportion, scaled by the transfer matrix 290 itself).

In some embodiments, system 10 produces a map of potentials on the heart wall while avoiding the use of an inverse solution, such as when voltages $V_i$ at points "i" on the heart wall are determined (e.g. via algorithm 255) by their linear relation to voltage values $W_k$ on the body surface, such as by using the equation (1) immediately herebelow:

$$V_i = \sum_k M_{ik} W_k \quad \text{Equation (1)}$$

Drive signals are applied to "k" surface electrodes ($SE_k$) and the response $V_i$ is measured on "i" heart-wall electrodes ($HW_i$). In the summation of equation (1), there is only one term, for which:

$$M_{ik} = \frac{V_i}{|\text{Drive Voltage}|}$$

Accordingly, $W_k$ is measured and $V_i$ is obtained from equation (1) by multiplication with $M_{ik}$ itself. In these embodiments, system 10 can include a minimum number of surface electrodes providing the drive signals k (e.g. electrodes $312_S$ and/or $322_S$ configured as drive electrodes), such as at least 3, at least 6, at least 9, or at least 12 surface electrodes.

In some embodiments, the applying of transfer matrix 290 by system 10 to a first set of recorded signals 313 comprises applying a ratiometric function of transfer matrix 290 to the first set of recorded signals 313. The ratiometric function can comprise an "identity function" for which the resultant set of recorded values (e.g. calculated patient information 95) are determined (e.g. solely by transfer matrix 290 itself). The ratiometric function can also be configured to linearly scale transfer matrix 290 as a "linear proportion function". Alternatively or additionally, the ratiometric function can be configured to nonlinearly scale transfer matrix 290 (e.g. as a "nonlinear proportion function").

In some embodiments, the applying of transfer matrix 290 by system 10 to a first set of recorded signals 313 comprises applying a nonlinear geometric function of transfer matrix 290 to the first set of recorded signals 313.

In some embodiments, system 10 transforms (e.g. using an inverse solution) the electrical activity measured by the internal electrodes to produce a second map of potentials on the heart wall. System 10 can be configured to produce a third map of potentials on the heart wall, based on the first map and the second map, wherein the third map is more accurate than the first or second maps alone. Alternatively, use of an internal electrode is avoided, and system 10 is configured to produce a map of cardiac wall potential data using surface electrodes only. For example, transfer matrix 290 can be determined using a patient P2, and the cardiac electrical activity calculated for a separate patient P1, such as when patient P2 has a similar heart size or other similar characteristics to those of patient P1. The degree of similarity between the patients P2 and P1 can be assessed, and correction factors employed to account for differences (e.g. differences in body weight, size, heart dimensions, and the like).

In some embodiments, system 10 records voltage information at a first, alpha location, and determines electrical activity information at a second, different, beta location. For example, recording electrodes 311 (e.g. positioned on the skin of the patient) can record voltages, and system 10 can produce calculated patient information 95 comprising electrical activity information at target locations 90 comprising locations within the patient, such as locations on and/or within a patient organ such as the heart or brain. In some embodiments, the electrical activity information comprises voltage information, surface charge information, and/or dipole density information, such as is described in applicant's co-pending U.S. patent application Ser. No. 16/533,028, titled "Method and Device for Determining and Presenting Surface Charge and Dipole Densities on Cardiac Walls", filed Aug. 6, 2019, and/or applicant's co-pending U.S. patent application Ser. No. 16/568,768, titled "Device and Method for the Geometric Determination of Electrical Dipole Densities on the Cardiac Wall", filed Sep. 12, 2019, the content of each of which is incorporated herein in its entirety for all purposes. In these embodiments, an inverse solution can be used to determine calculated patient information 95, such as an inverse solution used in conjunction with transfer matrix 290 to improve the accuracy of the calculated patient information 95. System 10 can use transfer matrix 290 to compensate for spatial and/or temporal anisotropy.

In some embodiments, system 10 comprises: device 100 including one or more electrodes configured to record electrical activity from inside the patient's heart (e.g. one or more electrodes $411_I$ and/or electrode-based functional elements $99_I$); one or more electrodes positioned on the patient's skin (e.g. via garment 50) configured to record electrical activity on the surface of the patient; and algorithm 255 configured to calculate electrical information of the heart (e.g. voltage information, dipole density information, and/or surface charge information). In these embodiments, algorithm 255 can calculate an inverse solution to determine the electrical information using the recorded electrical activity from inside the patient's heart and from the surface of the patient. In some embodiments, the inverse solution is constrained to (limited to) normal, strictly tangential and/or strictly scalar density-magnitudes of dipoles. In these embodiments, the additional recorded data (surface data) can be used to "doubly constrain" the inverse solution or provide a corroborating or correcting data set to improve accuracy of the inverse solution. Alternatively or additionally, the additional recorded data (surface data) constrains the inverse solution sufficiently such that the inverse solution can allow for directionally-unconstrained vector dipoles (i.e. linear combinations of normal dipoles and tangential dipoles). In some embodiments, the additional recorded data (surface-recorded data) can be used to calculate electrical information of the heart by applying algorithm 255 at locations of a heart surface (e.g. on a three-dimensional shell with no thickness). In some embodiments, the additional recorded data (surface-recorded data) can be used to calculate electrical information of the heart applying algorithm 255 within and/or throughout tissue, such as through or throughout the transmural thickness of one or more heart chambers, and/or within a three-dimensional structure that includes variations in tissue thickness representative of structural anatomy, such as myocardial tissue between the endocardium and epicardium, interatrial septum, interventricular septum, and the like. In some embodiments, the additional recorded data (surface data) can be used by algorithm 255 to improve the accuracy of the inverse solution at one or more cardiac locations, such as one or more left atrial locations such as locations proximate the pulmonary veins, the left atrial appendage, and/or the mitral valve. In some embodiments, the internal and surface recorded data can be recorded simultaneously and used by algorithm 255 to improve the modeling of the ventricular component of the electrical information, such as for V-wave (QRST) removal.

As described hereabove, system 10 can be configured to perform a localization procedure, such as a procedure that determines the position of one or more portions of device 100 and/or another device that has been inserted into the patient. In these embodiments, system 10 can be configured to improve the accuracy of the position information utilizing transfer matrix 290. In some embodiments, system 10 can be configured to improve the accuracy in real-time or at least near-real-time ("real-time" herein), throughout a patient procedure (e.g. a patient mapping and/or ablation procedure). In some embodiments, system 10 is configured to perform real-time updates of localization data, using skin placed electrodes (e.g. electrodes $311_S$, $321_S$, $411_S$, and/or electrode-based functional element $99_S$) and electrical information determined by continual transmitting and recording by internal and external electrodes.

In some embodiments, system 10 includes a distribution of electrodes which are configured for multiple purposes, such as multiple electrodes positioned via garment 50 on and/or proximate the patient's skin (herein "on the patient's skin") at particular locations relative to the patient's anatomy. In some embodiments, the multiple electrodes are used to determine electrical information related to the patient's heart, such as voltage maps, dipole density maps, and/or surface charge maps of a heart surface, such as is described herein. In some embodiments, one or more of the electrodes (e.g. electrodes 311, 321, and/or electrode-based functional elements 99) are configured to deliver electrical signals and/or electrical energy, such as to perform a localization procedure, to deliver cardiac pacing energy, deliver cardiac defibrillation energy, and/or deliver therapeutic energy. In some embodiments, the one or more electrodes are configured to provide an electric ground (e.g. a return path for one or more signals, such as a return path for delivery of ablation energy) and/or a reference signal (e.g. a reference voltage).

In some embodiments, system 10 includes a first set of one or more electrodes for positioning on the patient's skin (e.g. via garment 50) to perform a first function, and a second, different set of one or more electrodes for positioning on the patient's skin (e.g. via garment 50) to perform a second, different function. For example, one set of electrodes can comprise a size and/or set of materials configured to perform cardiac pacing and/or fibrillation, while a different set of electrodes comprises a size and/or set of material configured to record electrical signals.

In some embodiments, system 10 includes a set of multiple electrodes that are multiplexed (e.g. via a switching network) such that a first subset of one or more electrodes is used for a first function and one or more different additional subsets of one or more electrodes can be used for different functions. For example, one subset can be used to record signals to create a voltage, surface charge, and/or dipole density map of a heart surface, one subset can be used to create an ECG (e.g. an ECGi and a subset used for a 12-lead ECG), one subset can be used to pace the patient's heart; one subset can be used to defibrillate the patient's heart, one subset can be used as an electric ground, and/or one subset can be used as a reference signal. In some embodiments, subsets of electrodes for a particular function can be modified by an operator of system 10, such as a modification made during a procedure to improve recording and/or energy delivery.

In some embodiments, one or more functions of system 10 (e.g. localization, defibrillation, and/or other function described hereabove) can be optimized or at least improved ("optimized" herein) during a patient procedure, such as to adjust for patient-specific and/or environment-specific conditions. In these embodiments, system 10 can comprise multiple electrodes that are interconnected (e.g. "grouped") into one or more sets of electrodes, such as one or more electrode sets that each perform a function (e.g. a diagnostic function and/or a therapeutic function). In some embodiments, sets of particular electrodes (e.g. sets for particular functions) are pre-defined and/or automatically adjusted by system 10. Alternatively or additionally, sets of particular electrodes can be selected and/or adjusted by a user of system 10 (e.g. a clinician of the patient). Different sets can be configured to perform different functions. Additionally or alternatively, different sets can be configured to perform the same function, such as when a first set of electrodes is used to perform a function, after which a second set is used to perform the same function, such as to optimize the performance of that function. In some embodiments, a combination of multiple sets of electrodes are configured to perform a single function, such as multiple sets of one or more electrodes configured as "localization patches".

For example, system 10 can be configured such that sets of one or more electrodes are configured as localization patches, these patches being dynamically adjustable without having to remove and reapply electrodes. These sets of electrodes can be set and/or adjusted (e.g. electrodes at particular anatomical positions are selected or adjusted), such as an adjustment in which orthogonal axes are modified and/or additional axes are included. For example, in a cardiac procedure, a lateral shift of 1-2 pairs of sets of electrodes can be performed, such as to account for dextrocardia (heart is more rightward).

In another example, system 10 can be configured such that sets of one or more electrodes are configured as cardiac pacing and/or defibrillation electrodes, these sets of electrodes being dynamically adjustable to optimize pacing and/or defibrillation, without having to remove and reapply electrodes. In some embodiments, pacing and/or defibrillation electrode placement is chosen based on physician preference. In some embodiments, one or more pacing and/or defibrillation electrodes that are also used for a different function(s) are disconnected from other functional circuitry prior to delivering the pacing and/or defibrillation energy. For example, after delivery of pacing and/or defibrillation, system 10 can be configured to rapidly switch one or more of the electrodes (and/or other electrodes) to a mapping mode, such as to record heart electrical information soon after pacing and/or defibrillation, allowing the creation of maps of pacing recovery, defibrillation recovery, and/or arrhythmia onset (e.g. atrial fibrillation onset). Alternatively or additionally, system 10 can be configured to deliver electrical energy to a non-cardiac organ of the patient, such as a patient's brain, such as to treat a neurological condition such as epilepsy, migraine headaches, depression, and the like.

In another example, system 10 can be configured such that sets of one or more electrodes can be selected to deliver energy in a particular pattern, such as to optimize energy delivery to a location (e.g. the heart, the brain, and/or another organ of the patient). For example, one or more sets of energy-delivering electrodes can be switched and/or adjusted to successfully cardiovert a patient, and/or to prevent or at least reduce a seizure. In some embodiments, a pattern of electrodes is selected to reduce required energy delivery. In some embodiments, a spiral pattern of electrodes can be included. In some embodiments, a pattern of electrodes can be tuned (adjusted) based on mapped electrical activity (e.g. of the heart or brain) and/or the physiologic substrate (e.g. of the heart or brain).

In some embodiments, system 10 is configured to determine transmural conduction within heart tissue (e.g. endocardial to epicardial, and vice versa), such as when algorithm 255 analyzes data recorded by sensors placed on the skin of the patient (e.g. via garment 50, such as electrodes $311_S$, $321_S$, $411_S$, and/or electrode-based functional element $99_S$) as well as data recorded by sensors within the patient (e.g. via device 100, such as electrodes $311_P$, $321_P$, $411_P$, and/or electrode-based functional element $99_P$). Algorithm 255 can make the determination using one or more boundary conditions, such as the endocardial, epicardial, and/or pericardial voltage (e.g. as directly measured and/or indirectly determined by system 10). As described hereabove, algorithm 255 can utilize additional recorded data (e.g. surface data) to "doubly constrain" a mathematical transform (e.g. an inverse solution) and/or provide a corroborating or correcting data set to improve accuracy of output of algorithm 255.

Figure 1A:
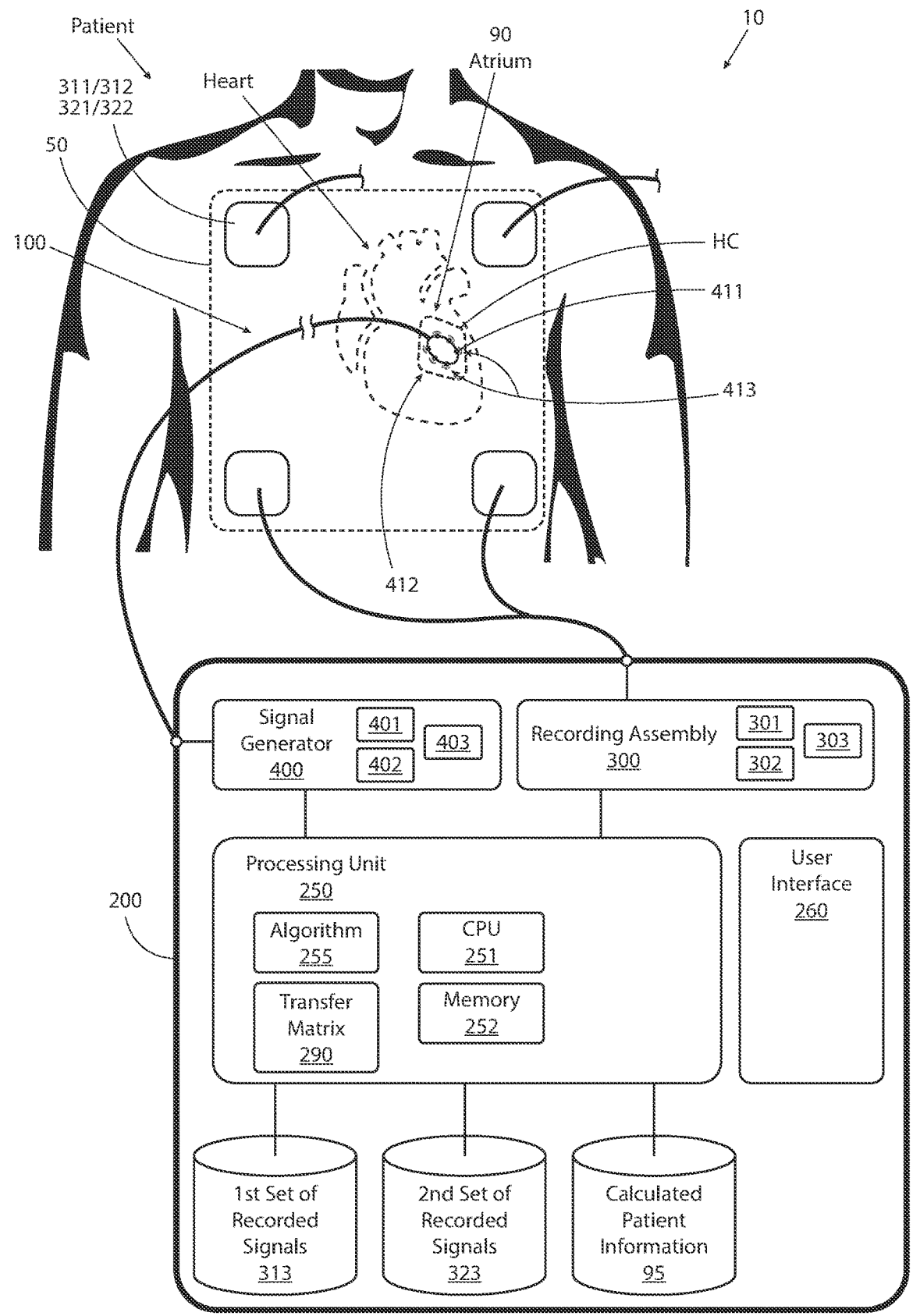
FIG. 1A illustrates a schematic view of a system for calculating information related to one or more parameters of a patient's heart, consistent with the present inventive concepts.

Referring now to FIG. 1A, a schematic view of a system for calculating information related to one or more parameters of a patient's heart is illustrated, consistent with the present inventive concepts. System 10 of FIG. 1A can be of similar construction and arrangement to system 10 of FIG. 1 described hereabove, and it can include similar components. In the embodiment of FIG. 1A, system 10 is arranged and configured to calculate patient information 95 that is related to a patient's heart, such as information related to one or more target locations 90 in the patient's left atrium. Patient information 95 can be determined using transfer matrix 290 and be based on signals 313 recorded by one or more recording electrodes 311 positioned at one or more skin-based recording locations 312. Recorded signals 313 can be recorded by recording assembly 300 (e.g. and stored in memory 252 of processing unit 250). Recording electrodes 311 can be included in patient garment 50, and/or patient garment 50 can be used simply as a template to position electrodes 311 in particular anatomical locations on the patient's skin.

In some embodiments, system 10 is configured to determine transfer matrix 290, such as when system 10 includes one or more drive electrodes 411 positioned at one or more drive locations 412 and configured to deliver drive signals 413 (e.g. drive signals 413 provided by signal generator 400). In these embodiments, a set of recording electrodes 321 are included and positioned at locations 322 to record signals 323. In the embodiment shown in FIG. 1A, drive electrodes 411 are positioned at drive locations 412 within the patient (e.g. drive electrodes 411 are included in an expandable cage or other distal portion of a body-inserted device 100, such as at a location within a chamber of the patient's heart) and recording electrodes 321 are positioned on the skin of the patient at locations 322. In some embodiments, recording locations 322 are the same or at least similar to recording locations 322 (e.g. recording electrodes 321 are the same or at least similar to recording electrodes 311) as shown in FIG. 1A. Alternatively, recording electrodes 321 comprise different electrodes and/or recording locations 322 comprise different locations than recording electrodes 311 and recording locations 312, respectively. Algorithm 255 can produce transfer matrix 290 based on an analysis of the recorded signals 323 compared to the drive signals 413.

Figure 2:
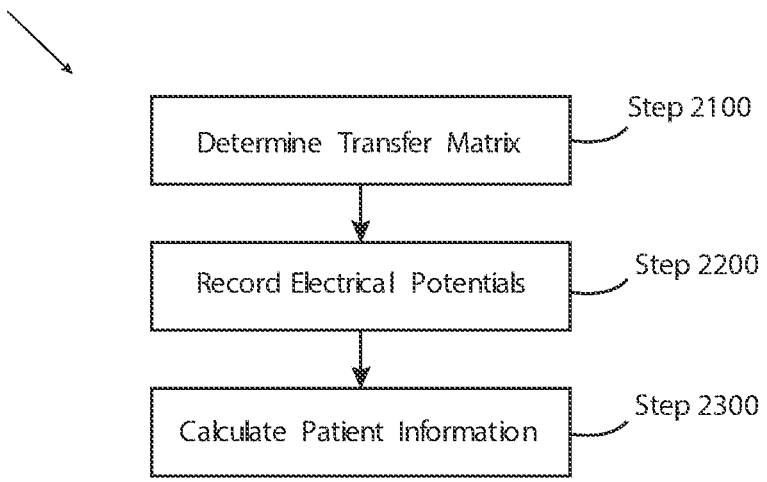
FIG. 2 illustrates a flow chart of a method for using a transfer matrix to calculate patient information based on recorded signals, consistent with the present inventive concepts.

Referring now to FIG. 2, a flow chart of a method of determining patient information at target locations is illustrated, consistent with the present inventive concepts. Method 2000 of FIG. 2 provides a method of recording electrical activity at one or more recording locations and applying a transfer matrix to the recordings to determine patient information at one or more target locations. Method 2000 will be described using system 10 and its various components described hereabove in reference to FIG. 1.

In STEP 2100, transfer matrix 290 is determined. Transfer matrix 290 can be determined based on information recorded from a single patient (e.g. patient P1 described hereabove in reference to FIG. 1), and/or multiple patients, (e.g. patients P1, P2 and/or other mammalian patients). Transfer matrix 290 can be determined by generating drive signals 413 from one or more recording locations 322 via a set of one or more recording electrodes 321, as described hereabove in reference to FIG. 1. In some embodiments, transfer matrix 290 is determined as described herebelow in reference to FIG. 3.

In STEP 2200, electrical potentials are recorded. For example, a first set of recording electrodes, recording electrodes 311, record electric potentials at a first set of recording locations, recording locations 312, to create a set of recorded signals, recorded signals 313 stored in console 200, such as is described hereabove in reference to FIG. 1.

In STEP 2300, patient information is calculated. For example, patient information 95 can be calculated for a set of target locations, such as target locations 90 comprising one or more locations on and/or within the patient. Patient information 95 can be calculated by applying transfer matrix 255 to the recorded signals 313, such as is described hereabove in reference to FIG. 1.

Referring now to FIG. 3, a flow chart of a method of determining a transfer matrix, and subsequently determining patient information at target locations using the transfer matrix is illustrated, consistent with the present inventive concepts. Method 3000 of FIG. 3 provides a method of determining a transfer matrix. The method further provides recording electrical activity at one or more recording locations, and applying the transfer matrix to the recordings to determine patient information at one or more target locations. Method 3000 will be described using system 10 and its various components described hereabove in reference to FIG. 1.

In STEP 3050, drive signals are emitted or otherwise delivered to tissue, such as via a set of one or more drive electrodes 411, from one or more drive locations 412. The drive signals 413 are recorded, such as via a set of one or more recording electrodes 321 from one or more recording locations 322, to create a set of recorded signals 323 which can be stored in console 200, such as is described hereabove in reference to FIG. 1.

In STEP 3100, transfer matrix 290 is determined based on the recorded signals 323 recorded in Step 3050.

In STEP 3200, electrical potentials are recorded. For example, a first set of recording electrodes, recording electrodes 311, record electric potentials at a first set of recording locations, recording locations 312, to create a set of recorded signals, recorded signals 313 stored in console 200, such as is described hereabove in reference to FIGS. 1 and/or 2.

In STEP 3300, patient information is calculated. For example, patient information 95 can be calculated for a set of target locations, such as target locations 90 comprising one or more locations on and/or within the patient. Patient information 95 can be calculated by applying transfer matrix 255 to the recorded signals 313, such as is described hereabove in reference to FIGS. 1 and/or 2.

The above-described embodiments should be understood to serve only as illustrative examples; further embodiments are envisaged. Any feature described herein in relation to any one embodiment may be used alone, or in combination with other features described, and may also be used in combination with one or more features of any other of the embodiments, or any combination of any other of the embodiments. Furthermore, equivalents and modifications not described above may also be employed without departing from the scope of the invention, which is defined in the accompanying claims.

What is claimed is:

1. A patient information processing system, comprising:
   a recording assembly configured to record electric potentials via a first set of recording electrodes located at a first set of recording locations on and/or within a patient to create a first set of recorded signals;
   a processing unit configured to calculate patient information for a set of target locations within the patient by applying a transfer matrix to the first set of recorded signals, wherein the transfer matrix comprises a characterization of electrical properties of tissue between the first set of recording locations and the set of target locations,
   wherein the recording assembly is further configured to record voltages of the patient at a second set of recording locations and the processing unit is further configured to determine electrical information at the first set of recording locations,
   wherein the calculated patient information is based on the output of an inverse solution, and the transfer matrix is applied to improve the quality of the calculated patient information, and
   wherein the system is configured to apply the transfer matrix to the first set of recorded signals by applying a nonlinear geometric function of the transfer matrix to the first set of recorded signals.

2. The system according to claim 1, wherein the transfer matrix accounts for spatial anisotropy and/or temporal anisotropy.

3. The system according to claim 1, wherein the calculated patient information comprises information selected from the group consisting of: electrical information; voltage information; surface charge information; tissue charge information; dipole density information; tissue density information; electrographic flow information; impedance information; phase information; and combinations thereof.

4. The according to claim 1, wherein the calculated patient information comprises tissue density information.

5. The system according to claim 4, wherein the tissue density information comprises information related to changes in tissue density over time.

6. The system according to claim 5, wherein the change in tissue density over time comprises changes caused by ablation of the tissue.

7. The system according to claim 1, wherein the transfer matrix comprises a characterization of electrical properties of tissue between the first set of recording locations and the set of target locations.

8. The system according to claim 1, wherein:
   the transfer matrix is modified over time; and/or
   the transfer matrix is modified based on at least one varying patient parameter, and/or
   the transfer matrix is modified to compensate for respiration of the patient, and/or
   the transfer matrix is modified to compensate for cardiac motion of the patient.

9. The system according to claim 8, wherein the system is further configured to monitor the at least one varying patient parameter.

10. The system according to claim 9, wherein:
    the monitoring comprises continuous monitoring of the at least one varying patient parameter; and/or
    the transfer matrix is modified continuously.

11. The system according to claim 9, wherein:
    the monitoring comprises intermittent monitoring of the at least one varying patient parameter; and/or
    the transfer matrix is modified intermittently.

12. The system according to claim 1, wherein the applying of the transfer matrix to the first set of recorded signals comprises the processing unit applying a linear geometric function of the transfer matrix to the first set of recorded signals.

13. The system according to claim 1, wherein the system is configured to gather patient physiologic data, and
    wherein the patient physiologic data comprises data selected from the group consisting of: physiologic cycle data; cardiac data; respiration data; patient medication data; skin impedance data; perspiration data; thoracic and/or abdominal cavity dimensional data; water weight data; hematocrit level data; wall thickness data; cardiac wall thickness data; and combinations thereof.

14. The system according to claim 1, wherein the system is further configured to perform a device localization procedure to determine device location information.

15. The system according to claim 1, further comprising:
    a signal generator configured to emit a set of drive signals via a set of drive electrodes located at a set of drive locations,
    wherein the recording assembly is configured to record the emitted drive signals via a second set of recording electrodes located at a second set of recording locations to create a second set of recorded signals, and wherein the processing unit is configured to determine the transfer matrix by comparing the second set of recorded signals to the emitted set of drive signals.

16. The system according to claim 15, wherein the transfer matrix is determined using the magnitude and/or phase of the second set of recorded signals.

17. The system according to claim 16, wherein the transfer matrix comprises a numerical scale factor based on a comparison of the magnitude and/or phase of the second set of recorded signals to the magnitude and/or phase of the set of drive signals.

18. The system according to claim 15, wherein the emitting of the set of drive signals and the recording of the emitted drive signals occur over at least one physiologic cycle of the patient.

19. The system according to claim 18, wherein the physiologic cycle comprises a cycle selected from the group consisting of: a cardiac cycle; a respiratory cycle; a pressure cycle; and combinations thereof.

20. The system according to claim 15, wherein the determining of the transfer matrix comprises calculating and/or selecting a standardized transfer matrix.

21. The system according to claim 20, wherein the standardized transfer matrix is selected based on a patient parameter.

22. A patient information processing system, comprising:
a recording assembly configured to record electric potentials via a first set of recording electrodes located at a first set of recording locations on and/or within a patient to create a first set of recorded signals;
a processing unit configured to calculate patient information for a set of target locations within the patient by applying a transfer matrix to the first set of recorded signals, wherein the transfer matrix comprises a characterization of electrical properties of tissue between the first set of recording locations and the set of target locations,
wherein the recording assembly is further configured to record voltages of the patient at a second set of recording locations and the processing unit is further configured to determine electrical information at the first set of recording locations, and
wherein the calculated patient information is based on the output of an inverse solution, and the transfer matrix is applied to improve the quality of the calculated patient information; and
a signal generator configured to emit a set of drive signals via a set of drive electrodes located at a set of drive locations,
wherein the recording assembly is configured to record the emitted drive signals via a second set of recording electrodes located at a second set of recording locations to create a second set of recorded signals, and
wherein the processing unit is configured to determine the transfer matrix by comparing the second set of recorded signals to the emitted set of drive signals, and
wherein the drive signals comprise:
a first drive signal from a first drive electrode at a first frequency; and
a second drive signal from a second drive electrode at a second frequency,
wherein the first frequency and the second frequency are different.

23. The system according to claim 22, wherein the first drive signal and the second drive signal are delivered simultaneously.

24. A patient information processing system, comprising:
a recording assembly configured to record electric potentials via a first set of recording electrodes located at a first set of recording locations on and/or within a patient to create a first set of recorded signals;
a processing unit configured to calculate patient information for a set of target locations within the patient by applying a transfer matrix to the first set of recorded signals, wherein the transfer matrix comprises a characterization of electrical properties of tissue between the first set of recording locations and the set of target locations,
wherein the recording assembly is further configured to record voltages of the patient at a second set of recording locations and the processing unit is further configured to determine electrical information at the first set of recording locations, and
wherein the calculated patient information is based on the output of an inverse solution, and the transfer matrix is applied to improve the quality of the calculated patient information; and
a signal generator configured to emit a set of drive signals via a set of drive electrodes located at a set of drive locations,
wherein the recording assembly is configured to record the emitted drive signals via a second set of recording electrodes located at a second set of recording locations to create a second set of recorded signals,
wherein the processing unit is configured to determine the transfer matrix by comparing the second set of recorded signals to the emitted set of drive signals, and
wherein the drive signals comprise:
a first drive signal from a first drive electrode at a first frequency; and
a second drive signal from a second drive electrode at a second frequency,
wherein the first frequency and the second frequency are delivered sequentially.

25. The system according to claim 24, wherein the first frequency and the second frequency are the same frequency.

26. A patient information processing system, comprising:
a recording assembly configured to record electric potentials via a first set of recording electrodes located at a first set of recording locations on and/or within a patient to create a first set of recorded signals;
a processing unit configured to calculate patient information for a set of target locations within the patient by applying a transfer matrix to the first set of recorded signals, wherein the transfer matrix comprises a characterization of electrical properties of tissue between the first set of recording locations and the set of target locations,
wherein the recording assembly is further configured to record voltages of the patient at a second set of recording locations and the processing unit is further configured to determine electrical information at the first set of recording locations, and
wherein the calculated patient information is based on the output of an inverse solution, and the transfer matrix is applied to improve the quality of the calculated patient information; and
a signal generator configured to emit a set of drive signals via a set of drive electrodes located at a set of drive locations,
wherein the recording assembly is further configured to record the emitted drive signals via a second set of recording electrodes located at a second set of recording locations to create a second set of recorded signals, wherein the processing unit is configured to determine the transfer matrix by comparing the second set of recorded signals to the emitted set of drive signals, wherein the determining of the transfer matrix comprises calculating and/or selecting a standardized transfer matrix based on a patient parameter, and wherein the patient parameter comprises a parameter selected from the group consisting of: gender; weight; height; body or body portion size; body mass index (BMI); thoracic cavity circumference; location of the esophagus; size of an atrium; filling of an atrial volume; atrial pressure; fat to water ratio; air to water to fat ratio; bone location; medications being taken; level of medication; electrolyte level; pH; pO2; pCO2; water weight; and combinations thereof.

\* \* \* \* \*

UNITED STATES PATENT AND TRADEMARK OFFICE
CERTIFICATE OF CORRECTION

| | | |
|---|---|---|
| PATENT NO. | : 12,178,582 B2 | Page 1 of 1 |
| APPLICATION NO. | : 17/275690 | |
| DATED | : December 31, 2024 | |
| INVENTOR(S) | : Gunter Scharf et al. | |

It is certified that error appears in the above-identified patent and that said Letters Patent is hereby corrected as shown below:

In the Claims

Column 44, Line 11, Claim 4, after the word "The" and before the word "according", please insert the word --system--.

Signed and Sealed this
Eleventh Day of February, 2025

Coke Morgan Stewart
*Acting Director of the United States Patent and Trademark Office*